US008041513B2

(12) United States Patent
Chait et al.

(10) Patent No.: US 8,041,513 B2
(45) Date of Patent: Oct. 18, 2011

(54) SYSTEMS AND METHODS INVOLVING DATA PATTERNS SUCH AS SPECTRAL BIOMARKERS

(75) Inventors: Arnon Chait, Bay Village, OH (US); Boris Y. Zaslavsky, Solon, OH (US)

(73) Assignee: Analiza, Inc., Bay Village, OH (US)

( * ) Notice: Subject to any disclaimer, the term of this patent is extended or adjusted under 35 U.S.C. 154(b) by 1188 days.

(21) Appl. No.: 11/641,611

(22) Filed: Dec. 19, 2006

(65) Prior Publication Data
US 2007/0198194 A1 Aug. 23, 2007

Related U.S. Application Data

(60) Provisional application No. 60/751,715, filed on Dec. 19, 2005.

(51) Int. Cl.
*G01N 33/48* (2006.01)
(52) U.S. Cl. ........................................................ 702/19
(58) Field of Classification Search .................... 702/19
See application file for complete search history.

(56) References Cited

U.S. PATENT DOCUMENTS

| | | | |
|---|---|---|---|
| 5,008,204 A | 4/1991 | Stehling | |
| 5,241,072 A | 8/1993 | Colon et al. | |
| 5,340,474 A | 8/1994 | Kauvar | |
| 5,734,024 A | 3/1998 | Zaslavsky | |
| 5,769,074 A | 6/1998 | Barnhill et al. | |
| 5,818,231 A | 10/1998 | Smith | |
| 5,948,750 A | 9/1999 | Garsky et al. | |
| 6,136,960 A | 10/2000 | Chait et al. | |
| 7,011,955 B1 | 3/2006 | Stemmler et al. | |
| 7,247,498 B2 | 7/2007 | Godec et al. | |
| 2002/0145425 A1* | 10/2002 | Ebbels et al. | ............... 324/309 |
| 2003/0162224 A1 | 8/2003 | Chait et al. | |
| 2004/0229375 A1 | 11/2004 | Chait et al. | |
| 2004/0236603 A1 | 11/2004 | Heller et al. | |
| 2006/0240416 A1 | 10/2006 | Banerjee et al. | |
| 2006/0255257 A1 | 11/2006 | Belgovskiy et al. | |
| 2006/0269964 A1 | 11/2006 | Chait et al. | |
| 2007/0128618 A1 | 6/2007 | Chait et al. | |
| 2008/0050831 A1 | 2/2008 | Chait et al. | |

FOREIGN PATENT DOCUMENTS

| | | | |
|---|---|---|---|
| WO | WO 99/10522 A1 | 3/1999 | |
| WO | WO 00/10674 A1 | 3/2000 | |
| WO | WO 01/55698 A1 | 8/2001 | |
| WO | WO 03/016883 A1 | 2/2003 | |
| WO | WO 03/042694 A2 | 5/2003 | |
| WO | WO 2004/111655 A1 | 12/2004 | |
| WO | WO 2005/008247 A2 | 1/2005 | |
| WO | WO 2005/008247 A3 | 1/2005 | |
| WO | WO 2006/124100 A2 | 11/2006 | |
| WO | WO 2007/027561 A2 | 3/2007 | |
| WO | WO 2008/005043 A2 | 1/2008 | |

OTHER PUBLICATIONS

Bodnar et al. "Exploiting the Complementary Nature of LC/MALDI/MS/MS and LC/ESI/MS/MS for Increase Proteome Coverage," J. Am. Soc. Mass Spectrom. (2003) vol. 14, pp. 971-979.*
Zaslavsky, "Aqueous Two-Phase Partitioning" (Book) Marcel Dekker, New York, Ch. 1-10 (1995).
Office Action from Canadian Application No. 2,466,663 dated May 6, 2010.
Office Action from Canadian Application No. 2,528,535 dated Mar. 15, 2010.
Office Action from European Application No. 04776693.6 dated May 11, 2010.
Office Action from U.S. Appl. No. 11/818,911 dated Jun. 23, 2010.
Office Action from U.S. Appl. No. 10/293,959 dated Jul. 7, 2010.
Durand et al. "Protein Glycosylation and Diseases: Blood and Urinary Oligosaccharides as Markers for Diagnosis and Therapeutic Monitoring" Clinical Chemistry 46:6, pp. 795-805 (2000).
Guzzetta "Reverse Phase HPLC Basics for LC/MA" an IonSource Tutorial, published Jul. 22, 2001.
Peracaula et al. "Altered glycosylation pattern allows the distinction between prostate-specific antigen (PSA) from normal and tumor origins" Glycobiology, vol. 13, No. 6, pp. 457-470, 2003.
Schena et al. "Parallel human genome analysis: Microarray-based expression monitoring of 1000 genes" Proc. Natl. Acad. Sci. vol. 93, pp. 10614-10619, Oct. 1996.
Singh et al. "Gene expression correlates of clinical prostate cancer behavior" Cancer Cell: Mar. 2002, vol. 1, pp. 203-209.
Takano et al. "Measuring the Solubility of Liquid Organic Compounds in Water" Journal of the Chemical Society of Japan, 1985, (11), pp. 2116-2119.
Office Action European Application No. EP 06851492 dated Mar. 31, 2009.
Office Action European Application No. EP02768567 dated Mar. 24, 2009.
Office Action Canadian Application No. 2,528,535 dated May 5, 2009.

(Continued)

*Primary Examiner* — Jerry Lin
(74) *Attorney, Agent, or Firm* — Wolf, Greenfield & Sacks, P.C.

(57) ABSTRACT

The present invention is generally related to the separation, fractionation, and/or characterization of molecules and/or biomolecules in one or more mixtures. After fractionation, different phases of a partitioning system can be analyzed via an analytical technique such as spectral analysis, chromatography, or the like, to produce a spectrum or other symbolic representation of the species after fractionation, and the spectra of the various fractions/phases compared to define a comparative spectrum as a marker or otherwise providing information about the sample, including such information that is independent of the original level of abundance of the molecules in the mixture. Comparative spectra of various samples can be compared to each other and/or to controls or reference spectra and/or comparative spectra to determine a variety of information. In some embodiments, the methods can be used for discovering and/or identifying patterns in a mixture of species and/or corresponding patterns of species in a second mixture, where each mixture of species originates from biological systems with different physiological conditions as markers associated with specific diagnostics, and can be used for screening for such markers once discovered and identified during diagnostics screening.

32 Claims, 7 Drawing Sheets

OTHER PUBLICATIONS

Office Action European Application No. 04776693 dated Oct. 10, 2008.
Office Action European Application No. 04776693 dated Oct. 15, 2007.
Office Action European Application No. 02795636 dated Nov. 14, 2005.
Office Action European Application No. 02795636 dated Feb. 8, 2007.
Office Action European Application No. 02795636 dated Oct. 27, 2008.
International Search Report and Written Opinion for PCT/US2006/048344 (filed Dec. 19, 2006) dated Apr. 24, 2008.
Office Action in U.S. Appl. No. 10/779,164 dated Jul. 31, 2009.
Office Action in U.S. Appl. No. 10/779,164 dated Feb. 25, 2010.
Sniegoski, P. "An Examination of the Concentration of Organic Components Water-Extracted From Petroleum Products" Water Research, vol. 9, pp. 421-423 (1975).
Stovsky, M., et al. "PSA/SIA: A New Highly Sensitive and Specific Structure-Based Assay for Prostate Cancer" (presentation), AUA NC 82$^{nd}$ Annual Meeting, Chicago, IL, Sep. 24-27, 2008.
Takano, Japanese Chemistry Association Journal, 1985 (11), p. 2116-2119.
Yan, X. "Detection by ozone-induced chemiluminescence in chromatography"; Journal of Chromatography, 842 (1999), pp. 267-308.
Everberg et al., "Protein pre-fractionation in detergent-polymer aqueous two-phase systems for facilitated proteomic studies of membrane proteins," *J. Chromatogr A* (2004) 1029:113-124.
Office Action from U.S. Appl. No. 10/293,959 dated Jul. 17, 2007.
Office Action from U.S. Appl. No. 10/293,959 dated Jun. 25, 2008.
Office Action From U.S. Appl. No. 10/293,959 dated Apr. 28, 2009.
Canadian Office Action in 2,466,663, dated May 6, 2010.
Canadian Office Action in 2,528,535, dated Mar. 15, 2010.
Takano et al. "Measuring the Solubility of Liquid Organic Compounds in Water" Journal of the Chemical Society of Japan, 1985, (11), pp. 2116-2119.
QSAR Introduction (web pages; pub. date unknown; last accessed Jul. 2, 2007).
Richon, A. et al., "An Introduction to QSAR Methodology," (web page; pub. date unknown; last accessed Jul. 2, 2007).
Albertsson P. et al., "Aqueous Two-Phase Separations," *Bioprocess Technol.*, vol. 9, pp. 287-327, (1990).
Andrews, T. et al., "Affinity gel electrophoresis as a predicative technique in the fractionation of transgenic sheep milk proteins by affinity aqueous two-phase partitioning," *Biotechnol Lett* 22:1349, (2000).
Arnoldi, A et al., "Lipophilicity-Antifungal Activity Relationships for Some Isoflavonoid Phytoalexins," *J. Agric. Food Chem.*, 1990, vol. 38, pp. 834-838.
Atkinson, L. et al., "Trypsin and α-Chymotrypsin Partitioning in Polyethylene Glycol/Maltodextrin Aqueous-Two-Phase Systems," *Food Bioprod. Proc.*, Jun. 1994, vol. 72, pp. 106-112.
Berggren, K. et al., "Substitutions of surface amino acid residues of cutinase probed by aqueous two-phase partitioning," *BBA* 2000, 1481, pp. 317-327.
Bevan, C. et al., "A High-Throughput Screening Method for the Determination of Aqueous Drug Solubility Using Laser Nephelometry in Microtiter Plates," *Anal. Chem.*, 2000, vol. 72, pp. 1781-1787.
Chait, A. "From Structure to Signature," 8$^{th}$ Annual SBS Conference & Exhibition, Sep. 22-26, 2002, Netherlands Congress Centre, The Hague, The Netherlands.
Chait, A. "HTS Technology for Analysis of Structural Signatures of Biomolecules: Methodology and Applications," California Separation Science Society, WCBP 2002, 6$^{th}$ Symposium on the Interface of Regulatory and Analytical Sciences for Biotechnology Health Products, Jan. 27-30, 2002.
Guiliano, K., "Aqueous Two-Phase Protein Partitioning Using Textile Dyes as Affinity Ligands," *Anal. Biochem.*, 1991, vol. 197, pp. 333-339.
Gulyaeva, N. et al., "Relative hydrophobicity of organic compounds measured by partitioning in aqueous two-phase systems," *Journal of Chromatograph B*, 2000, vol. 743 pp. 187-194.
Harboe, M. et al., "Generation of Antibodies to the Signal Peptide of the MPT83 Lipoprotein of *Mycobacterium tuberculosis*," *Scan. J. Immunol.*, 2002, vol. 55, pp. 82-87.
Kohwi, Y. et al., "Amphipathic Lipid-Bound Protein Antigens in Mouse Bladder Carcinomas Detected by a Monoclonal Antibody," *Biochemistry*, 1984, vol. 23, pp. 5945-5950.
Kuboi, K. et al., "Evaluation of Surface Hydrophobicities of Proteins Using Hydrophobic Interaction with Non-ionic Surfactants in Aqueous Two-Phase Partitioning Systems," *Kagaku Kogaku Ronbunshu*, vol. 19, pp. 446-453.
Müller, W. et al., "Real and Pseudo Oxygen Gradients in Ca-Alginate Beads Monitored During Polarographic $Po_2$-Measurements Using Pt-Needle Microelectrodes," *Biotechnology and Bioengineering*, 1994, vol. 44, pp. 617-625.
Platt, D.E. et al., "QSAR in grossly underdetermined systems: Opportunities and issues," *IBM Journal of Research and Development*, vol. 45, 2001 (web page).
Program listing of the Society of Biomolecular Screening 2002, Session 2A Technical Program for the 8$^{th}$ Annual SBS Conference & Exhibition, Sep. 22-26, 2002, Netherlands Congress Centre, The Hague, The Netherlands.
Program listing of the Well-Characterized Biologics Conference 2002, California Separation Science Society, WCBP 2002, 6$^{th}$ Symposium on the Interface of Regulatory and Analytical Sciences for Biotechnology Health Products, Jan. 27-30, 2002.
Sakurai, A. et al., "Ligand- and Nuclear Factor-Dependent Change in Hydrophobicity of Thyroid Hormone $β_1$ Receptor," *Thyroid*, 1998, vol. 8, No. 4, pp. 343-352.
Takano, J. et al., "Solubility Measurement of Liquid Organic Compounds in Water," *CAS Online*, 105:60254, (1985) vol. 11, pp. 2116-2119.
Zaslavsky, A. et al., "A New Method for Analysis of Components in a Mixture without Preseparation: Evaluation of the Concentration Ratio and Protein-Protein Interaction," *Analytical Biochemistry*, 2001, vol. 296, pp. 262-269.
International Search Report for PCT/US02/26019.
International Preliminary Examination Report for PCT/US02/26019.
International Search Report for PCT/US02/36519.
International Search Report dated Nov. 23, 2004 for PCT/US2004/019343.
Written Opinion for PCT/US2004/019343.
Office Action mailed Jun. 29, 2006 from U.S. Appl. No. 10/293,959.
Office Action mailed Dec. 5, 2006 from U.S. Appl. No. 10/293,959.

* cited by examiner

SYSTEMS AND METHODS INVOLVING DATA PATTERNS SUCH AS SPECTRAL BIOMARKERS

RELATED APPLICATIONS

This application claims the benefit of U.S. Provisional Patent Application Ser. No. 60/751,715, filed Dec. 19, 2005, entitled "Systems and Methods Involving Spectral Biomarkers," by Chait, et al., incorporated herein by reference.

FIELD OF INVENTION

The present invention is generally related to the characterization of physical samples from the analysis of at least one component or species of the sample. In some specific embodiments, the invention relates to fractionation of species within a samples and comparative analysis of different fractions to define comparative data, which can be compared to other, similar data to provide information regarding the sample and/or a species within the sample.

BACKGROUND

Many diseases and/or other pathological processes or conditions are caused by dysfunction and/or disregulation of certain proteins. These disease-related proteins may have their structures altered, relative to their "normal" or "wild-type" counterparts, and/or may be expressed in larger (up-regulated expression) or smaller (down-regulated expression) quantities in a given disease state, relative to "normal" physiological conditions. In some cases, proteins having altered structure and/or function may be used as markers associated with a particular human or animal disease, for instance, as a diagnostic for earlier detection of the disease, or the like. In many cases, the particular protein(s) of relevance to a given pathological process of a disease or other condition are unknown. Identification of such protein(s) would be useful for development of new diagnostic tests, or the like.

A general approach to the identification and characterization of protein markers is based on the analysis of protein compositions of samples of biological material (biological fluids, such as blood, serum, plasma, cerebrospinal fluid, tissues, cells, etc.) using high resolution separation techniques. For instance, proteins isolated from control and experimental samples or populations can be subjected to proteolytic cleavage, and their cleavage products identified using liquid chromatography (LC) coupled with tandem mass spectrometry (LC-MS-MS). Many protein separation techniques are based on multi-dimensional separation of proteins from a sample, typically by two-dimensional gel electrophoresis (2-DE) or two-dimensional high-performance liquid chromatography (2D-HPLC). The two-dimensional (2-D) protein maps for pathological samples may be obtained and compared with those for reference samples; positions of proteins observed as "spots" on (2-DE) maps or as "peaks" on 2D-HPLC maps can be compared, and those that are present (or absent) in the maps obtained from pathological samples but absent (or present) in the maps obtained from the reference samples may be judged as being likely to correspond to pathologically relevant proteins. Additionally, quantities of proteins estimated as intensities of the spots (or peaks) may be evaluated and compared between the pathological and reference samples. Those that are significantly different may be considered as pathologically relevant in some cases.

It has also been recently established that a pattern of the presence/absence and/or the relative quantities of multiple proteins (a "signature") may also be of diagnostic relevance, where the proteins judged to be of interest are identified by peptide mapping and/or mass spectrometry. Mathematical or statistical techniques, such as pattern recognition techniques, can be used to analyze the pattern produced by these experimental techniques and produce a diagnostic classification. However, this approach is often highly inefficient, for example, due to the inherent necessity of analyzing all of the proteins in a given sample, whereas only a small portion of the proteins may have any pathological relevance.

Several different methods for reducing the analytical complexity of protein mixtures have been developed. These methods are typically based on fractionation of the original mixture prior to 2D analysis by gel electrophoresis or 2D-HPLC. One such method is the separation of proteins by the technique of free-flow electrophoresis. However, this technique, while fractionating the original protein mixture, may result in multiple 2D analysis of simplified fractions, i.e. while reducing the complexity of analysis and improving resolution, it inherently greatly increases the number of samples where further analysis is required.

Another method is fractionation based on the affinity of proteins to different natural ligands and/or pharmacological compounds; however, this approach, while allowing separation of proteins according to protein functions, may result in a large increase in the number of samples for further analysis, and often requires additional knowledge or presumption concerning the differences between the samples.

One disadvantage of most fractionation techniques is that they generally cannot preserve protein-protein or protein-ligand interactions. Differences among biological interactions are often important for elucidating and detecting changes among samples. Additionally, most of the fractionation techniques rely on separation due to a fixed physical attribute, such as molecular size or net charge. While these attributes may be very important for distinguishing among biomolecules in a complex mixture, they generally do not cover all of the potential differences between biomolecules representing, e.g., normal vs. disease states, differences in configuration etc. Another important disadvantage of present fractionation techniques is related to their inability to separate mixtures based on differences between structural changes in, e.g., glycosylation patterns and/or conformational changes. These changes are often important for identifying proteins that either participate in and/or are the result of a disease state. For example, if a protein is misfolded as a result of genetic mutation, the net charge and size of the protein may not vary significantly, and more importantly, the protein's expression level might be the same for the underlying normal vs. disease states. Finally, natural genetic variability among individuals can significantly contribute to a very large scatter in the expression levels (concentrations) of biomolecules in a biological sample. This variability generally necessitates use of statistically large number of samples to robustly detect differences innate to a particular pathological condition, rather than to genetic variability. Natural genetic variability is often a significant hindrance in implementing protein marker based diagnostics due to reduction of the sensitivity and/or specificity of the diagnostic test.

While significant advances in the field of molecular and/or sample characterization have been made, improvements are therefore needed to add specificity, versatility, convenience, and/or improve efficiency.

SUMMARY OF THE INVENTION

The present invention is generally related to the separation, fractionation, and/or characterization of a mixture of molecules and/or biomolecules or other species. For example, in some embodiments, the present invention provides systems and methods for the analysis and characterization of mixtures of biomolecules, complexes comprising biomolecules, molecules which interact with biomolecules, and/or analogous species thereof. For example, differences in overall patterns of analyses of mixtures of biomolecules may indicate protein markers of a disease and/or a physiological state of a living organism.

The subject matter of this application may involve, in some cases, interrelated products, alternative solutions to a particular problem, and/or a plurality of different uses of a single system or article.

One aspect of the invention is directed to a method of determining a characteristic of a plurality of species. The method, according to one set of embodiments, includes acts of exposing a plurality of species to at least first and second interacting components defining at least a first phase and a second phase, respectively, of a first system that includes at least two phases, obtaining a first spectral data pattern comprising cumulative spectral information from a plurality of species of the first phase of the system after exposure, obtaining a second spectral data pattern comprising cumulative spectral information from a plurality of species of the second phase of the system after exposure and/or cumulative spectral information from a plurality of the plurality of species prior to exposure to the system, and deriving comparative spectral information from comparison of at least a portion of the first spectral data pattern with at least a portion of the second spectral data pattern, to determine a characteristic of a plurality of species.

In one embodiment, the invention involves developing and using methods for utilizing the effects of differences in relative measures of interaction of species with different phases of multi-phase systems, e.g. fractionation or separation, for example via multi-phase partitioning, of two, three, or more mixtures, which may reflect differences between the mixtures related to the structural and/or functional characteristics of a mixture of molecules and/or molecules which interact with such molecules. These techniques can be used, for instance, to identify unique patterns of such markers using mass spectrometry or other analyses in samples, and/or to use such patterns of markers for diagnostics and other related applications.

In one aspect, the invention is a method of determining a characteristic of a plurality of species. In one set of embodiments, the method includes acts of exposing a plurality of species to, and causing the plurality of species to interact differently relative to each other upon said exposure to, at least first and second interacting components defining at least a first phase and a second phase, respectively, of a first system that includes at least two phases; obtaining a first spectral data pattern comprising cumulative spectral information from a plurality of species of the first phase of the system after exposure, which spectral data pattern is representative of the effect of such of the relative measures of interaction of the species with the different phases; obtaining a second spectral data pattern comprising cumulative spectral information from a plurality of species of the second phase of the system after exposure, and/or cumulative spectral information from a plurality of the original plurality of species; and deriving comparative spectral information from at least a portion of the first spectral data pattern and the second spectral data pattern to determine a characteristic of a plurality of species.

In another set of embodiments, the method includes acts of partitioning a plurality of species between a first phase and a second phase of a partitioning system that includes at least two phases; obtaining a first spectral data pattern comprising cumulative spectral information from a plurality of species of the first phase of the system after partitioning; obtaining a second spectral data pattern comprising cumulative spectral information from a plurality of species of the second phase of the system after partitioning, and/or cumulative spectral information from a plurality of the original plurality of species; and deriving comparative spectral information from at least a portion of the first spectral data pattern and the second spectral data pattern to determine a characteristic of a plurality of species.

In another aspect, the invention involves determining a physiological condition of a biological system. In one embodiment, a method for doing so involves determining a comparative pattern from a mixture of species of a sample from a biological system, where the comparative pattern is derived from patterns of data obtained from analysis of at least first and second interacting components defining at least a first phase and a second phase, respectively, of a first partitioning system. From the process of determining the comparative pattern between the mixture of species and the first and second interacting components of the first partitioning system, the physiological condition of the biological system can be determined.

In another embodiment, the method involves determining a physiological condition of a biological system by determining a difference between the comparative pattern described herein that was obtained from a biological system and a corresponding comparative pattern representative of a reference condition of the biological system, without knowledge of the chemical or biological identity of the individual species in the mixture of species that result in such patterns.

In another embodiment, a method involves determining a physiological condition of a biological system by determining a difference and/or similarity between a first property and/or value of a property associated with a comparative pattern obtained from the biological system and the comparative patterns obtained from at least one sample with at least one reference condition.

In yet another embodiment, the method involves determining the physiological condition of a biological system by determining the difference and/or similarity between mathematically or statistically processed analysis patterns obtained from the biological system, and similarly mathematically or statistically processed comparative patterns of relative measures of interaction obtained from at least one sample with at least one reference condition.

In another aspect, the invention relates to a method of identifying one or more tools for physiological analysis. In one embodiment, the method involves determining a comparative pattern between the data patterns obtained from analyses of species comprising a first mixture of species and at least first and second interacting components defining at least a first phase and a second phase, respectively, of a first partitioning system. A comparative pattern also determined likewise between the species comprising a second mixture of species, corresponding to the species of the first mixture of species, and the first system. A difference is determined in the comparative pattern of the species of the first mixture, versus the comparative pattern of the species of the second mixture, with the first system. Based upon this difference, a first system is selected as a tool for determining a physiological condition of a biological system. Alternatively, or in addition, the comparative pattern of the species comprising the first mixture and the comparative pattern of the species comprising the second mixture are selected for determining a physiological condition of a biological system.

The invention, in still another aspect, is directed to a method of determining at least one characteristic of a plurality of species. The method, according to one set of embodiments, includes acts of exposing a plurality of species to an aqueous partitioning system including at least first and second phases; obtaining, using mass spectroscopy, a first spectral data pattern comprising cumulative spectral information from a first sample of one or more species associated with the first phase of the aqueous partitioning system; obtaining, using mass spectroscopy, a second spectral data pattern from one or more of the following: (1) a second sample of one or more species associated with the second phase of the aqueous partitioning system, or (2) a portion of the plurality of species prior to the exposing step; and comparing at least a portion of the first spectral data pattern with at least a portion of the second spectral data pattern to determine at least one characteristic of a plurality of species.

The method, in another set of embodiments, includes acts of exposing a plurality of species to at least first and second interacting components to at least partially separate the plurality of species; treating a first sample of the at least partially separated plurality of species, using mass spectroscopy, to produce a first spectral data pattern; treating one or more of the following, using mass spectroscopy, to produce a second spectral data pattern: (1) a second sample of the at least partially separated plurality of species that is not identical to the first sample, or (2) a portion of the plurality of species prior to the exposing step; and comparing at least a portion of the first spectral data pattern with at least a portion of the second spectral data pattern to determine at least one characteristic of a plurality of species.

In still another set of embodiments, the methods exposing a plurality of species to an aqueous partitioning system including at least first and second phases; obtaining a first data pattern comprising cumulative information from a first sample of one or more species associated with the first phase of the aqueous partitioning system; obtaining a second data pattern comprising cumulative information by treating one or more of the following: (1) a second sample of one or more species associated with the second phase of the aqueous partitioning system, or (2) a portion of the plurality of species prior to the exposing step; and comparing at least a portion of the first data pattern with at least a portion of the second data pattern to determine at least one characteristic of a plurality of species.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figure, which is schematic and not intended to be drawn to scale. In the figure, each identical or nearly identical component illustrated is typically represented by a single numeral. For purposes of clarity, not every component is labeled, nor is every component of each embodiment of the invention shown where illustration is not necessary to allow those of ordinary skill in the art to understand the invention. In the figures.

DETAILED DESCRIPTION

Figure 1:
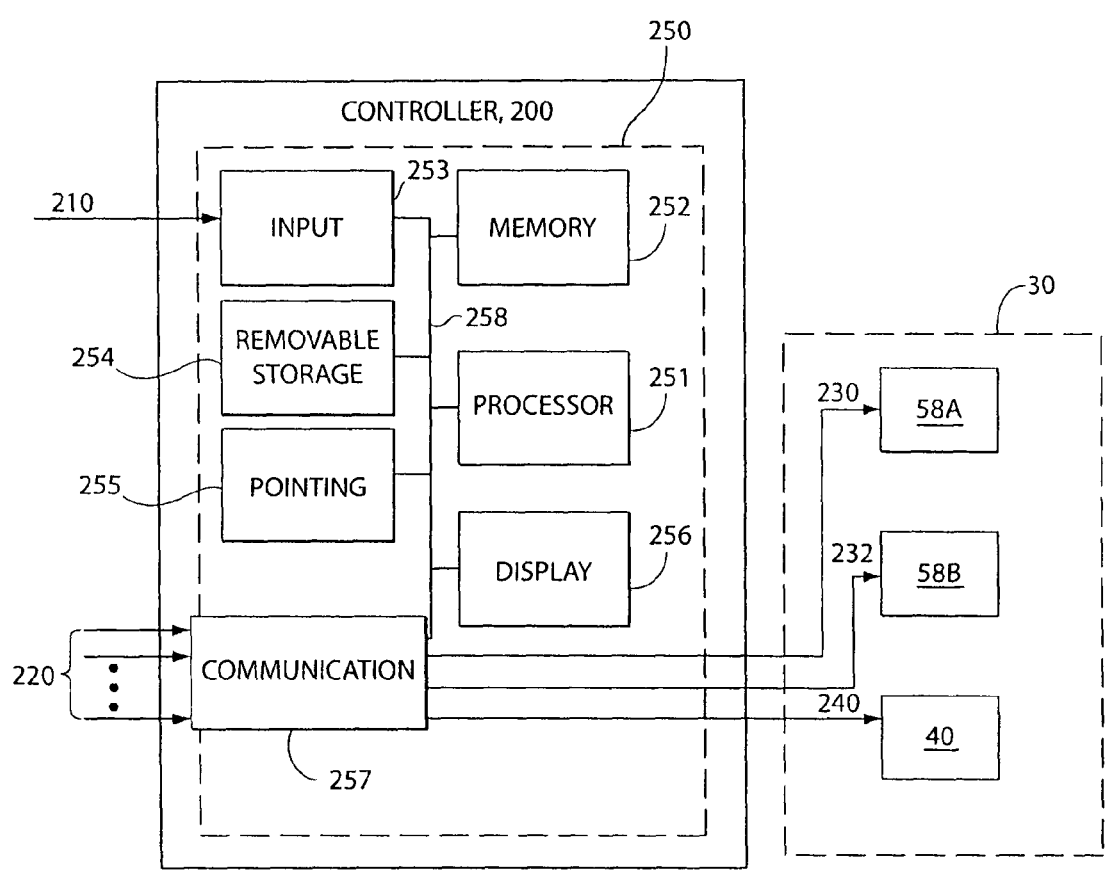
FIG. 1 is a schematic block diagram of a process for conducting the determining and using the patterns of the relative measures of interaction according to one embodiment of the present invention.
Figure 2:
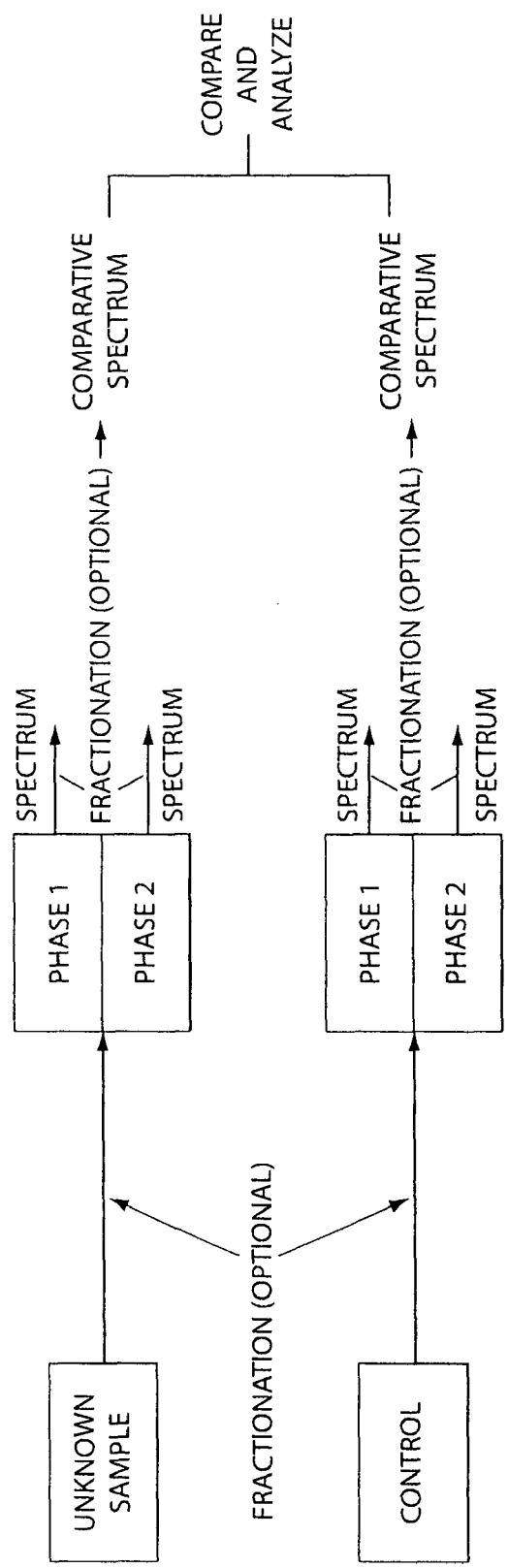
FIG. 2 is a schematic block diagram of comparison of comparative mass spectral information from partitioning systems providing information to the user, in accordance with the invention.

The present invention is generally related to the interaction of a plurality of molecules or other species with media that can cause separation of at least some of the molecules or species from each other, and treatment of at least one portion of molecules/species resulting from separation to define a pattern. The pattern can be compared to a pattern from another portion of molecules/species resulting from separation, and/or from a pattern obtained from the original plurality of molecules or other species prior to separation, resulting in characterization of the plurality of molecules and/or biomolecules or other species, and/or characterization of a condition associated with an entity associated with the molecules/species with or without any specific characterization of any molecules or biomolecules, etc. The separation media can include multi-phase partitioning systems or other separation materials discussed below. The mixture may be partially or fully separated. In some embodiments, the present invention provides systems and methods for the detection, identification, and/or characterization of differences between properties or behavior of corresponding patterns of data, for example, measures of interaction of species in the mixture. Any technique may be used to generate the pattern, for example spectral analysis techniques such as mass spectroscopy, NMR spectroscopy, UV and/or visible spectroscopy, etc. The plurality of molecules may include biomolecules and/or molecules able to interact with biomolecules. The pattern may be produced using samples of the mixture (before or after separation), depending on the comparison to be achieved.

One aspect of the invention involves use of spectral data (as a pattern) obtained from, e.g., a mass spectrometer, obtained from a sample or a fraction of a sample, for example a sample of biological origin, where the sample is first allowed to interact with an interacting system. The interacting system interacts preferentially with some of the species in the sample to result in at least one (and sometimes more than one) fraction of the sample that is different from the original sample. The spectral data is then compared with either another spectral data obtained from a second fraction of the same sample which was allowed to interact with the same interacting system, or from the spectral data of the sample itself.

However, it should be understood that the invention is not limited to the use of only spectral data. In general, any method of treatment of a sample that can be used to produce a data pattern can be used. For example, a portion of a sample or fraction of a sample may be treated to produce a data pattern using any suitable technique, for example, NMR spectroscopy, UV and/or visible spectroscopy, IR spectroscopy, Raman spectroscopy, fluorescence spectroscopy, mass spectroscopy, chromatography (e.g., liquid chromatography, HPLC, chromatographic elution profile analyses, etc.), GPC, ELIZA, scintillation counting, etc. In some cases, the data itself may be treated to produce a data pattern, e.g., by mathematical processing, data transformation, data smoothing, noise filters, etc. Accordingly, it should be noted that when discussions herein refer to "spectral data" or "comparative spectra," this is by way of example only, and other data patterns or comparative data patterns described herein may also be used, in other embodiments of the invention.

In one aspect, the invention involves partitioning and in some cases, following partitioning, the partitioning components can be subjected to spectral analysis such as mass spectral analysis, or the like, or other suitable methods for producing a data pattern, without the need to analyze spectra of different components and without the need, in certain embodiments, to attempt to identify characteristics of those components (although this can be done in some embodiments). Spectral data or other data patterns of different components or phases, and/or species within them, can be compared in some embodiments to define a comparative spectrum or pattern which, in and of itself, can be a marker associated with the mixture of species and/or can reveal information about the mixture of species. This information can include information about the condition of an entity from which the species was derived, for example, a medical condition and/or a physiological condition of a patient when the comparative spectrum or pattern is compared to a reference comparative spectrum or pattern defining a control. The comparative spectrum or pattern can be derived in some cases from the spectra or other data pattern of the components or phases using one or more mathematical operations, such as subtraction, division, multiplication or other transformation. In one embodiment, a comparative spectrum or pattern is obtained by a point-by-point division of the data pattern of the components or phases, since a division is also a normalization operation. A normalization operation in the present context refers to cancellation or removal of the absolute level of the data pattern attributable to the underlying protein, protein fragment, or peptide that resulted in a specific peak or other specific information in the two or more patterns being compared. Thus, a comparative spectrum or pattern that is obtained by dividing the data patterns of components or phases using point-by-point division only exhibits relative changes between the affinity of the underlying proteins to each of the phases and not to their absolute quantities in the original sample.

Other signal processing techniques and transformations can be used to pre- or post-process the data pattern before or after construction of the comparative pattern. Such techniques include, but are not limited to, data smoothing, noise filters, interpolation, etc. of the spectra, with or without transformations such as Fourier or wavelet transforms, etc., and with or without the use of digital or other filters.

For example, a control can be established by withdrawing a sample from a reference entity, such as a blood sample from a healthy patient (any other sample such as urine, plasma, and those known in the art can be used and/or further treated prior to use according to standard techniques). The sample can be subjected to fractionation in a multi-phase partitioning system (or any other technique disclosed herein). Where a two-phase partitioning system is used, at least a portion or portions of the first and second phases (or, optionally, more phases, if more phases exist) can be subjected to spectral analysis (or other data patterning technique disclosed herein) and their spectra (or other data pattern) compared to create a comparative spectrum. Alternatively, or in addition, the original sample prior to partitioning can be subjected to spectral analysis and its spectral data compared to one or more items of spectral data from the first and/or second phases to create a comparative spectrum. In some of these arrangements, any number of spectra of the mixture prior to partitioning, and any number of phases after the partitioning can be obtained. In some cases, at least two spectral data are compared to obtain information defining the control (optionally in combination with other information such as temperature, blood pressure, or the like). The comparative spectrum can, optionally, be stored for later use, for example stored as a paper printout of the spectral comparison, electronically stored in a computer or on any other known storage medium.

Where there is a question as to whether a particular entity exhibits a particular condition, for example, whether a patient has a particular physiological condition, then a sample (e.g., an analogous, similar, or identical sample as that of a control) can be withdrawn from the entity and subjected to systems that can at least partially separate the sample (e.g., a partitioning system). The data may be analyzed using the data from the partitioning phase or phases and/or the data pattern of the original, pre-partitioning mixture, and then compared (e.g., by forming a comparative spectrum). The comparative spectrum of the unknown can be compared to the comparative spectrum of a control to determine whether the sample substantially deviates from the control, or is essentially the same as the control, which can give indication as to whether the sample indicates disease in a patient or not. The control can be, of course, that of a healthy patient or that of a patient having any of a number of physiological dysfunctions or diseases. Alternatively, two or more controls can be used defining a healthy state and/or any of a number of dysfunctional states and the comparative spectrum or pattern from partitioning of the unknown sample can be compared to any or all of these controls to determine a state of the entity from which the sample was taken. In practice, multiple comparative spectra or patterns originating from different entities that exhibit the same dysfunctional state can be averaged to form a composite comparative spectrum or pattern.

In some embodiments, the methods can be used for discovering and/or identifying patterns in a mixture of species and/or corresponding patterns of species in a second mixture, where each mixture of species originates from biological systems with different physiological conditions as markers associated with specific diagnostics, and can be used for screening for such markers once discovered and identified during diagnostics screening.

The following documents are incorporated herein by reference in their entirety: U.S. Pat. No. 6,136,960, issued Oct. 24, 2000, entitled "Method for Evaluation of the Ratio of Amounts of Biomolecules or Their Sub-populations in a Mixture," by Chait et al.; PCT Publication No. WO 03/042694, published May 22, 2003 entitled "Characterization of Molecules," by A. Chait, et al.; U.S. Patent Application Ser. No. 60/478,645, filed Jun. 13, 2003, entitled "Systems and Methods for Characterization of Molecules," by A. Chait, et al.; U.S. Patent Application Ser. No. 60/561,945, filed Apr. 14, 2004, entitled "Systems and Methods for Characterization of Molecules" by Chait, et al.; International Patent Application No. PCT/US04/19343, filed Jun. 14, 2004, entitled "Systems and Methods for Characterization of Molecules," by A. Chait, et al.; U.S. Patent Application Ser. No. 60/634,586 filed Dec. 9, 2004, entitled "Spectral and Other Analysis of Partitioned Samples," by A. Chait, et al.; and U.S. Patent Application Ser. No. 60/751,715, filed Dec. 19, 2005, entitled "Systems and Methods Involving Spectral Biomarkers," by A. Chait, et al.

DEFINITIONS

As used in the specification and the appended claims, the singular forms "a," "an," and "the" include plural referents unless the context clearly dictates otherwise. Thus, for example, reference to "a biomolecule" can include mixtures of biomolecules, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

"Analyte," "analyte molecule," or "analyte species" refers to a molecule, for example, a macromolecule, such as a polynucleotide or polypeptide, whose presence, amount, and/or identity are to be determined.

"Antibody," as used herein, means a polyclonal or monoclonal antibody. Further, the term "antibody" includes, but is not limited to, intact immunoglobulin molecules, chimeric immunoglobulin molecules, or Fab or F(ab')$_2$ fragments. Such antibodies and antibody fragments can be produced by techniques well known in the art, which include, for example, those described in Harlow and Lane (*Antibodies: A Laboratory Manual*, Cold Spring Harbor Laboratory, Cold Spring Harbor, N.Y. (1989)), Kohler et al. (*Nature* 256: 495-97 (1975)), each incorporated herein by reference. Correspondingly, antibodies, as defined herein, also include single chain antibodies (ScFv), which may comprise linked $V_H$ and $V_L$ domains and which may retain the conformation and the specific binding activity of the native idiotype of the antibody. Such single chain antibodies are well known in the art and can be produced by standard methods. See, e.g., Alvarez et al., *Hum. Gene Ther.* 8: 229-242 (1997)). The antibodies of the present invention can be of any isotype, for example, IgG, IgA, IgD, IgE, or IgM.

"Aqueous," as used herein, refers to the characteristic properties of a solvent/solute system wherein the solvating substance has a predominantly hydrophilic character. Examples of aqueous solvent/solute systems include those where water, or compositions containing water, are the predominant solvent. In one embodiment, an aqueous material is miscible in water, and does not form a separate, identifiable phase apart from water after being left undisturbed for a day under ambient conditions (e.g., at 1 atm and room temperature, about 25° C. (Note that water is miscible in itself.)

A "partitioning system," as used herein, refers to any material having at least two phases, sections, areas, components, or the like, at least two of which can interact differently with at least one species to which they are exposed. For example, a partitioning system can include different areas of a solid surface, which can interact differently with a particular molecule exposed to the different sections (e.g., as in liquid chromatography or HPLC, etc.), a multi-phase system such as a multi-phase liquid system, e.g., an aqueous/non-aqueous system or an aqueous multi-phase system (defined below) to which one or more species can be exposed and optionally dissolved, at least some of which species can interact differently with different phases. For example, a particular species may have a greater affinity for one phase rather than another phase to the extent that a multi-phase partitioning system can isolate a species from a mixture, or cause a species to partition at least in some way differently between the phases. Where a two-phase system is described herein, it is to be understood that more phases can be used.

"Aqueous multi-phase system," as used herein, refers to an aqueous system which includes greater than one aqueous phase in which an analyte species can reside, and which can be used to characterize the structural state of the analyte species according to the methods described herein. For example, an aqueous multi-phase system can separate at equilibrium into two, three, or more immiscible phases. Aqueous multi-phase systems are known in the art, and this phrase, as used herein, is not meant to be inconsistent with accepted meaning in the art. Examples of various aqueous multi-phase systems, and their compositions, are described more fully below.

"Cumulative spectral information" means spectral information including input from a plurality of species, e.g., a spectrum (which can be a mass spectrum report) representing a mixture of species.

An "interacting component" means a component, such as a phase of a multi-phase system, or a component of a chromatography column or other composition able to cause separation, that can interact with a species and provide information about that species (for example, an affinity for the species). Multiple interacting components, exposed to a species, can define a system that can provide a "relative measure of interaction" between each component and the species. An interacting component can be solid or liquid, aqueous or non-aqueous, can be polymeric, organic (e.g. a protein, small molecule, etc.), inorganic (e.g. a salt), a surfactant, or the like, or any combination thereof. A set of interacting components can form a system useful in and in part defining any experimental method which is used to characterize the structural state of a species such as an analyte species according to the methods described herein. Typically, a system of interacting components can measure the relative interaction between the species and at least two interacting components.

An aqueous multi-phase system is an example of a system of interacting components, and it is to be understood that where "aqueous system" or "aqueous multi-phase system" is used herein, this is by way of example only, and any suitable system of interacting components can be used. Where aqueous two-phase and aqueous multi-phase systems are described herein, it is to be understood that other systems, as used herein, systems analogous to those comprising only aqueous solutions or suspensions can be used. For example, an aqueous two-phase system can include non-aqueous components in one or more phases that are not liquid in character. In this aspect, multi-phase systems also refers to related techniques that rely on differential affinity of the biomolecule to one media versus another, where the transport of the biomolecule between one medium and, optionally, another medium occurs in an aqueous or non-aqueous environment. Examples of such multi-phase systems include, but are not limited to, HPLC columns or systems for liquid-liquid partition chromatography or other forms of chromatography, as are known to those of ordinary skill in the art, where one phase may be a solid phase and another phase may be a liquid which carried species proximte the solid phase, and different affinity among various species for the solid and/or liquid phases can cause separation. It should be understood that the invention is not limited to aqueous multi-phase systems; in some cases, a system having a single, non-partitioned phase may be used; for example, two or more interacting components may define a solvent containing a plurality of species, and the components may be at least partially separated (although there may not necessarily be a clear division between the separated components, e.g., with respect to concentration, etc.)

"Relative measure of interaction," with reference to a particular species as used herein, means the degree to which the species interacts with another species or with a phase of a multi-phase system in a relative sense. For example, a particular species may have a greater affinity for one phase of a multi-phase system rather than another phase or phases, and the degree to which it interacts with or resides in, that phase, as opposed to other phases, defines its relative measure of interaction. Relative measures of interaction, in the context of the present invention, are generally determined in a ratiometric manner, rather than an absolute manner, although in some cases, the absolute manner can be used. As a non-limiting example, where a species can interact with each phase of a two-phase system but resides more preferably in one than the other, the present invention typically makes use of information as to the ratio of concentration of the species in each of the two phases, or in one of the phases and the original sample, but not necessarily of the absolute concentration of the species in either phase. In other cases, the interaction can be an interaction based not upon residence of a particular species within a particular solvent or fluid carrier, but upon interaction with a solid surface, such as a solid phase of a chromatography column, where the relative measure manifests itself in elution time, and/or can involve geometric or spatial interaction such as a particular species interaction with a porous substrate as opposed to that of a different species or a different substrate. In some cases, the relative measure of interaction includes more than one type of interaction.

"Partition coefficient," as used herein, refers to the coefficient which is defined by the ratio of chemical activity or the concentrations of a species in two, three, or more phases of a multi-phase system at equilibrium, or the ratio of chemical activity or the concentration of a species in one phase of a multi-phase system at equilibrium and the corresponding species in the original sample. For example, the partition coefficient ("K") of an analyte in a two-phase system is defined as the ratio of the concentration of analyte in the first phase to that in the second phase. For multi-phase systems, there may be multiple partition coefficients, where each partition coefficient defines the ratio of species in first selected phase and a second selected phase. It will be recognized that the total number of partition coefficients in any multi-phase system is typically equal to the total number of phases minus one. As used herein, the term "partition coefficient" also can refer to the ratio of the peak height at a specific m/z (mass-to-charge ratio) location from the analysis of the mixture of species in the first phase of a two-phase system to the corresponding height at the same specific m/z location from the analysis of the mixture of species in the second phase of the same two-phase system, or to the peak height ratio at a specific elution time in a chromatographic analysis between samples from two, three, or more different phases of such a system.

For heterogeneous phase systems, an "apparent partition coefficient," as used herein, refers to a coefficient which describes information obtained from alternative techniques that is correlated to the relative partitioning between phases. As a non-limiting example, if the heterogeneous two-phase system used is an HPLC column or other chromatography column, this "apparent partition coefficient" can be the relative retention time for the analyte. It will be recognized by those of ordinary skill in the art that the retention time of an analyte in a chromatography column, in many cases, reflects the average partitioning of the analyte between a first, mobile phase and a second, immobile phase. Also, it will be recognized that other, similarly determinable properties of analytes can also be used to quantify differences in physical properties of the analytes (e.g. in other techniques) and are, therefore, suitable for use as apparent partition coefficients.

"Bind," as used herein, means the well understood receptor/ligand binding, as well as other nonrandom association between an a biomolecule and its binding partner. "Specifically bind," as used herein, describes a binding partner or other ligand that does not cross-react substantially with any biomolecule other than the biomolecule or biomolecules specified. Generally, molecules which preferentially bind to each other are referred to as a "specific binding pair." Such pairs include, but are not limited to, an antibody and its antigen, a lectin and a carbohydrate which it binds, an enzyme and its substrate, and a hormone and its cellular receptor. Examples of binding mechanisms include, but are not limited to, covalent, ionic, van der Waals, hydrogen, or the like.

As generally used, the terms "receptor" and "ligand" are used to identify a pair of binding molecules. Usually, the term "receptor" is assigned to a member of a specific binding pair, which is of a class of molecules known for its binding activity, e.g., antibodies. The term "receptor" is also preferentially conferred on the member of a pair that is larger in size, e.g., on lectin in the case of the lectin-carbohydrate pair. However, it will be recognized by those of skill in the art that the identification of receptor and ligand is somewhat arbitrary, and the term "ligand" may be used to refer to a molecule which others would call a "receptor." The term "anti-ligand" is sometimes used in place of "receptor."

"Molecule-molecule interaction," such as a biomolecule-biomolecule interaction, a protein-protein interaction, and the like, means an interaction that typically is weaker than "binding," i.e., an interaction based upon hydrogen bonding, van der Waals binding, London forces, or other non-covalent interactions that contribute to an affinity of one molecule for another molecule, which affinity can be assisted by structural features such as the ability of one molecule to conform to another molecule or a section of another molecule. Molecule-molecule interactions can involve binding, but need not.

"Biomolecule," as used herein, means a molecule typically derived from an organism, and which typically includes building blocks including nucleotides, and the like. Non-limiting examples include peptides, polypeptides, proteins, protein complexes, nucleotides, oligonucleotides, polynucleotides, nucleic acid complexes, saccharides, oligosaccharides, carbohydrates, lipids as well as combinations, enantiomers, homologs, analogs, derivatives and/or mimetics thereof.

"Species," as used herein, refers to a molecule or collection of molecules. For example, an inorganic chemical, an organic chemical, a biomolecule, or the like may be a species. In the present invention, species generally are biomolecules.

"Corresponding species," as used herein, means at least two different species that are identical chemically or, if they differ chemically and/or by molecular weight, differ only slightly. Non-limiting examples of corresponding species include structural isoforms of proteins, proteins or other molecules that are essentially identical but that differ in binding affinity with respect to another species or plural species, have different higher-order structure, e.g., differing in secondary or tertiary structure but not differing or not differing significantly in chemical sequence. In general, corresponding species are species that may be arranged differently (isoforms, isomers, etc.) but are composed of the same or essentially the same chemical building blocks.

"Detectable," as used herein, refers the ability of a species and/or a property of the species to be discerned. One example method of rendering a species detectable is to provide further species that bind or interact with the first species, where the species comprise(s) a detectable label. Examples of detectable labels include, but are not limited to, nucleic acid labels, chemically reactive labels, fluorescence labels, enzymatic labels and radioactive labels.

As used herein, the term "determining" generally refers to the analysis of a species, for example, quantitatively or qualitatively, and/or the detection of the presence or absence of the species. "Determining" may also refer to the analysis of an interaction between two or more species, for example, quantitatively or qualitatively, and/or by detecting the presence or absence of the interaction.

"Mimetic," as used herein, includes a chemical compound, an organic molecule, or any other mimetic, the structure of which is based on, or derived from, a binding region of an antibody or antigen. For example, one can model predicted chemical structures to mimic the structure of a binding region, such as a binding loop of a peptide. Such modeling can be performed using standard methods (see, for example, Zhao et al., *Nat. Struct. Biol.* 2: 1131-1137 (1995)). The mimetics identified by methods such as this can be further characterized as having the same binding function as the originally identified molecule of interest, according to the binding assays described herein. Alternatively, mimetics can also be selected from combinatorial chemical libraries in much the same way that peptides are. See, for example, Ostresh et al., *Proc. Natl. Acad. Sci. U.S.A.* 91: 11138-11142 (1994); Dorner et al., *Bioorg. Med. Chem.* 4: 709-715 (1996); Eichler et al., *Med. Res. Rev.* 15: 481-96 (1995); Blondelle et al., *Biochem. J.* 313: 141-147 (1996); or Perez-Paya et al., *J. Biol. Chem.* 271: 4120-6 (1996).

"Solid support," as used herein, means the well-understood solid material to which various components of the invention are physically attached, thereby immobilizing the components of the present invention. The term "solid support," as used herein, means a non-liquid substance. A solid support can be, but is not limited to, a membrane, sheet, gel, glass, plastic or metal. Immobilized components of the invention may be associated with a solid support by covalent bonds and/or via non-covalent attractive forces such as hydrogen bond interactions, hydrophobic attractive forces and ionic forces, for example.

"Structure," "structural state," "configuration," or "conformation," as used herein, all refer to the commonly understood meanings of the respective terms, for example, as they apply to biomolecules such as proteins and nucleic acids, as well as pharmacologically active small molecules. In different contexts, the meaning of these terms will vary, as is appreciated by those of skill in the art. The structure or structural state of a molecule refers generally not to the building blocks that define the molecule but the spatial arrangement of these building blocks. The configuration or confirmation typically defines this arrangement. For instance, the use of the terms primary, secondary, tertiary, or quaternary, in reference to protein structure, have accepted meanings within the art, which differ in some respects from their meaning when used in reference to nucleic acid structure (see, e.g., Cantor and Schimmel, *Biophysical Chemistry*, Parts I-III). Unless otherwise specified, the meanings of these terms will be those generally accepted by those of skill in the art.

"Physiological conditions," as used herein, means the physical, chemical, or biophysical state of an organism. As most typically used in the context of the present invention, physiological condition refers to a normal (e.g., healthy in the context of a human or other organism) or abnormal (e.g., in a diseased state in the context of a human or other organism) condition.

"Pattern," as used herein, means a sequence of physical properties of species, or a combination of physical properties and other properties.

"Corresponding pattern," as used herein, means a second pattern that is typically obtained from a different sample of biological system or systems, and is comprised of the same sequence of physical or other properties, such that each location in the sequence possesses the same value of the descriptor, whether numerical or categorical in nature.

"Marker" as used herein, is a pattern of physical properties of species (e.g., a spectrum of m/z values obtained from mass spectrometry experiments of a mixture of species) that can be a carrier of information regarding the structural or physiological state of a biological environment within which it resides. A pattern of such physical properties can also be mathematically or statistically processed, condensed, transformed, or represented otherwise. A "processed marker," as used herein, is such a processed pattern, but as used herein, marker is used to alternatively designate the pattern of physical properties or the processed pattern of such properties, depending on the particular context. A marker can exhibit at least two different properties or values of a specific property or properties (e.g., structural conformation, binding affinity for another species, etc., but not solely different amounts of the species) that correspond to and that represent information regarding the two or more physiological states of environments within which they reside. For example, a marker may be a pattern obtained from a series of proteins, some of which are structurally modified between a first state representative of a healthy system within which it resides, and a second structural state (e.g., different conformations) representative of a disease system within which it resides. As used herein, a marker is also a comparative pattern that can be a carrier of information regarding a physiological state of a biological environment within which it resides, and/or a combination of such patterns and other information related to other properties.

"Spectral data" means any information, whether visible, recorded on paper, recorded electronically, or the like, relating to application of one or more spectral techniques to a sample, such as mass spectral investigation, infrared spectral investigation, UV and/or visible spectroscopy, NMR spectroscopy, or any other sequence of data obtained from sample analysis, in which the independent variable could include wavelength, elution time, etc.). Such spectral analysis could be performed by those of ordinary skill in the art using no more than routine skill.

Spectral data is one example of a data pattern, which is not limited to techniques in which the sample is interrogated vs. electromagnetic wavelength. A data pattern includes any sequence of analysis data obtained by other techniques, e.g., by chromatographic techniques that produce data streams vs. elution time rather than vs. wavelength, by NMR, etc.

"Comparing," in the context of spectra or spectral data (or other data pattern), means any type of comparison of any section or sections of the spectral data (or other data pattern).

For example, two typical printouts from a mass spectrometer can be compared side-by-side and a human can observe the height of one or more mass spectral peaks of each spectrum and make a notation as to comparison between those peaks, or can observe numbers associated with computer analysis representing mass-to-charge ratios associated with such peaks and compare these numbers. Alternatively, a computer can be programmed to compare various mass-to-charge peaks of various mass spectra to each other and to produce a comparative spectrum, or comparative spectral information, representing such comparison. Comparative spectral information may define, therefore, a number representing a difference in two spectra or other data patterns, and/or the number can define a ratio of the peak height or extent of two different spectra at a particular mass-to-charge ratio location (with the example of mass spectral data). Alternatively, a comparative spectrum can record differences in two or more data patterns at a plurality of spectral data points, that is, in the case of mass spectra a plurality of peaks at specific mass-to-charge ratios, recorded either as differences or ratios between the two spectra. As a further example, all data points of two mass spectra can be compared, either as differences between peaks at specific mass-to-charge ratios of each spectra or ratios between each, and displayed as a series of numbers or as a new spectral printout, or displayed any other way, where an observer or a machine (e.g., processor) can observe and/or analyze this data and thereby observe and/or record differences between different samples from which each spectrum was derived. All such spectral data and comparative spectra can be obtained with or without analysis of the data of the type that would lead to identification of any one or more species of the sample from which the spectral data was obtained. The data pattern could also be first mathematically processed, transformed to another domain, e.g., using Fourier or wavelet transforms, and the processed or transformed data could be compared to other spectra using techniques known to those skilled in the art, including simple mathematical operations, data reduction techniques such as eigenvalue analysis and alike. The use of comparison of spectra and the term "comparative spectrum" generally involves at least two data patterns of the same sample, at least one of which was obtained by interacting the sample with a multi-phase system. The action of comparison generally does not involve simply normalizing the data pattern, e.g., to obtain a baseline as customarily done in spectrometric or chromatographic analyses. The comparative spectrum is also generally derived in such a way that it does not depend on the concentration of species comprising the original sample, and may not necessarily carry information regarding the concentration or levels of abundance of the species in the original sample.

"Comparative spectral data" can be similarly derived from IR Spectra, UV/Vis spectra, and the like, as well as from a sequence of data points in time obtained, e.g., from a chromatographic elution profile. Those of ordinary skill in the art are familiar with comparative spectral data in connection, at least, with UV/Vis and IR Spectra, and a variety of techniques for recordation and/or display of such data. It is to be emphasized that, in connection with the invention, spectral data and/or comparative spectral data can be obtained and/or derived, in connection with a particular sample or samples, at any one or a number of data points associated with the spectra (any number of mass-to-charge ratios, wavelengths, elution times, etc.).

Embodiments

Recent advances in the study of spectral analysis, e.g., mass-spectrometry patterns of proteins and mixtures obtained from serum or other biological fluid, have demonstrated that one does not need to explicitly identify the proteins that differ between two samples to be able to distinguish between them. (It is to be understood that, anywhere in this application that a particular spectral technique is described, e.g., mass spectrometry, the particular spectral technique can be substituted by any other spectral or chromatographic technique, for example, as disclosed herein. In one particular set of embodiments of the invention, mass spectrometry is employed.) Thus, in some aspects, using signal pattern techniques, the differences in spectra can be expressed in mathematical terms that capture the pattern of the mixture (a "data pattern") without requiring their identification. Instead of identifying differences between samples by detecting changes in the concentration levels of specific proteins (biomarkers) or other species, the patterns representing the entire mixtures of proteins or other species in the samples are compared and subsequently used to classify the samples. These techniques are especially sensitive to changes in concentration levels that are not related to the, e.g., pathological or physiological changes that correspond to the samples under analysis. For certain applications, e.g., diagnostics of relatively rare diseases in general populations, the required level of specificity and sensitivity can be very high. Such high performance levels, coupled with inherent sensitivity of pattern recognition techniques to unrelated changes in concentration levels in the samples, can be addressed using certain systems and methods of the present invention. Pattern recognition-based methods as described in the present invention are inherently insensitive to absolute levels of expression, and may result in much more reliable patterns. Moreover, such patterns could be more closely correlated with the underlying differences between the samples. As mentioned, such comparative techniques are not limited only to mass spectroscopy data, but can also be applied to any data pattern that is produced in association with one or more species of a sample, for example, NMR spectroscopy, UV and/or visible spectroscopy, chromatography (e.g., liquid chromatography or HPLC), GPC, ELIZA, etc.

The state of a molecule or other species (e.g., a molecular aggregate, a multi-subunit protein, etc.), such as a biomolecule, can be affected by many factors including, but not limited to, changes in the chemical structure (e.g., addition, deletion or substitution of amino acids in proteins, covalent modification by chemical agents or cleavage by chemical or thermal degradation, addition or deletion of carbohydrates to the structure, etc.), interactions with one or more other species such as biomolecules or ligands, or the like. The evaluation of different states can be used as one method of determining the potential effectiveness of different molecules (or other species), condition of the molecules, condition or state of an environment (e.g., a mixture of species) within which the molecule or species resides, and the like.

The present invention involves, in some embodiments, the investigation of the state of molecules. The invention is described in the context of studies involving biomolecules and/or molecules able to interact with biomolecules, but the invention can apply to essentially any molecular species and/or interaction, whether biological, biochemical, chemical, or other species, and those of ordinary skill in the art will understand how the invention can be used in the context of non-biological molecules. It is to be understood that whenever "biomolecules" is used in the description of the invention, any non-biological molecule can also be used or studied.

In one aspect, the present invention involves techniques for determining information about the composition of a mixture of biomolecules (or other species) and/or molecules which interact with biomolecules. The mixture may originate from biological material, such as human clinical sample or other biological fluid, tissue, cells, a subject, etc., and/or the mixture may be a synthetic mixture. The mixture can come from a biological system which, as used herein, means a human or non-human mammal, including, but not limited to, a dog, cat, horse, cow, pig, sheep, goat, chicken, primate, rat, and mouse, other animals (e.g., frog), or a bacteria, virus, fungus, or of plant origin. The mixture may be taken from any suitable source within the human or other animal, for example, from tissue biopsies, whole blood, serum or other blood fractions, urine, ocular fluid, saliva, cerebro-spinal fluid, fluid or other samples from tonsils, lymph nodes, needle biopsies, etc.

The invention also relates, in some cases, to developing and determining characteristics (quantitative and/or qualitative) of a mixture that are obtained, for example, via processing using multi-phase partitioning or other separation techniques as described herein (e.g., chromatography), which can reflect certain structural and/or functional characteristics of biomolecules or molecules that interact with biomolecules in the original mixture. These characteristics can be used, for example, for establishing relationships between the composition of the mixture and the physiological state of the biological source of the mixture e.g., the state of health or disease of a subject. These characteristics can also be used to design experimental conditions for subsequent fractionation of the mixtures into subsets enriched in the molecule(s) of interest for the purpose of the analysis, while simultaneously reducing the total number of different molecule(s) in some cases. The separation may be full or partial, i.e., one or more species is present in a higher concentration in the subset, relative to the overall sample, but other species may still be present in the subset. The systems and methods of the present invention can also be useful for detecting, classifying, and/or predicting changes in a mixture of biomolecules or molecules that interact with biomolecules. For example, the mixture may be a synthetic mixture, or a mixture associated with a particular disease or physiological state of a living organism, cells, tissues, or biological liquids. The systems and methods of the present invention can also be used to detect changes to a one or more molecules or biomolecules in a biological mixture, and these changes could further be used, in some embodiments, to detect and classify a diagnostic that is related to such changes. However, in one embodiment, the systems and methods of the present invention are not used to simply remove a subset of species of the original mixture prior to analysis, even though such fractionation could be accomplished as a pre- (or post-) processing step of the mixture prior to (or subsequent to) interacting the mixture with a multi-phase system and deriving a comparative spectrum in the manner described herein.

Examples of such changes in a mixture can be the differences in properties of a pattern of species of the mixture, such as those related to differences in the species conformation, structure, and/or interaction tendency with respect to another molecule or molecules (e.g., its binding affinity or other interaction characteristic with respect to another molecule or molecules, or other species). For example, if the mixture includes proteins or other biomolecules, such changes may be induced through primary sequence modification, by degradation of the proteins or other biomolecules through chemical, thermal, or other degradation mechanisms, by interaction with other molecules and/or biomolecules, by interaction with low molecular weight compounds (e.g., hormones, peptides, vitamins, cofactors, etc.), by changes in the relative content or concentration of the constituents of the mixture, by reactions such as enzymatic reactions, by specific changes such as phosphorylation or glycosylation, etc. The systems and methods of the present invention can be used, in some cases, to detect, analyze and/or characterize biological species, including but not limited to, polypeptides, proteins, carbohydrates, nucleic acids, polynucleotides, lipids, and/or sterols, and mixtures or derivatives thereof, e.g., for the purpose of detection of, or onset of, a particular disease or physiological state, monitoring its progress, treatment, etc.

Comparison and classification steps involved in the invention can make use of additional information not necessarily related to (not directly derived from) the analytical methods of the invention. For example, blood pressure, temperature, blood glucose level, and/or essentially any other measurable physiological condition can be used in conjunction with techniques of the invention to analyze one or more physiological conditions.

In some embodiments of the invention, a plurality of species (molecules, biomolecules, etc.) is exposed to at least first and second interacting components, which may at least partially separate or "partition" the plurality of species, e.g., into a first portion and a second portion having a different composition than the first portion. For example, the first portion may be enriched in a first species (or a first conformation of a first species), while the second portion may be deficient in the first species or conformation. Such separation may be partial or total, in some cases. In some cases, the system is a partitioning system, as disclosed herein. Non-limiting examples include aqueous/non-aqueous partitioning systems, aqueous multi-phase partitioning system, liquid chromatography, HPLC, column liquid-liquid partition chromatography (LLPC), a heterogeneous two-phase system, a multiphase heterogeneous system, etc.

Multiple partitioning and/or other separation steps can take place in some embodiments of the invention so that additional information and/or sensitivity can be obtained. For example, prior to determining comparative patterns of species in each of two or more different mixtures, and following partitioning of both mixtures in two, three, or more partitioning systems of identical (or nearly identical) composition, a quantity of the first and/or the second interacting components of both systems containing the mixtures can be further introduced into a second set of two identical (or nearly identical) systems with at least two interacting components. Then, partitioning of both second sets of systems for both mixtures can take place, and comparative patterns of species in each mixture can be determined and used as described herein. As another non-limiting example, a mixture may first be subjected to chromatography, followed by partitioning (or vice versa).

It will be recognized by those of ordinary skill in the art that these biological species can be found in any suitable form, for example, in the form of extracts from natural sources, biological liquids, cell and tissue samples, bacteria, virus or fungus, collections of molecules generated by combinatorial chemical or biochemical techniques and combinations thereof, synthetically created, etc.

In one embodiment, the present invention provides a method to determine certain conditions under which variations among samples representing different compositions (or mixtures of species) could be detected, i.e., determining a set of criteria and/or system components as a "tool," or a part of a tool, to determine information. For example, the ability of a multi-phase system to determine a comparative pattern of species can serve as an important tool or component of such a tool. Specifically, as one non-limiting example, the partitioning of the constituents of a sample between two phases having different chemical or biochemical affinities or other characteristics, such as solvent structures, may separate the constituents by their relative affinity for media of different properties or composition. This separation technique thus can include or, alternatively, can be unlike those typically used in proteomics or similar techniques, e.g., 2D gel electrophoresis, in which charge and size differences are the two dimensions used to separate the constituents of a sample. In some cases, e.g., for many applications in proteomics, the present invention provides the ability for performing sequential and/or serial partitioning, with either the same of different conditions, which may result in additional amplification or differences in the fractionated samples. These patterns of physical properties of species comprising such fractions may be further analyzed in some cases using techniques such as mass spectrometry. However, in the context of the present invention, it is not necessarily the intent of such operations to simply fractionate or remove some species comprising the mixture, but to provide for means to derive a comparative spectrum that can be independent of information regarding the concentration or abundance levels of the original species in the mixture.

As mentioned herein, aqueous multi-phase (e.g., two-phase) partitioning systems are well-suited for use in many embodiments of the invention, but other partitioning systems can be used as well, according to other embodiments. Thus, where "aqueous two-phase partitioning" or "aqueous multi-phase partitioning" is used, it is to be understood that other systems can be used, for example, aqueous/non-aqueous two-phase partitioning, non-aqueous/non-aqueous two-phase partitioning, liquid chromatography, etc. Partitioning of a biopolymer in aqueous two-phase systems may depend on factors such as its charge, size, three-dimensional structure, type, topography of chemical groups exposed to the solvent, etc. For instance, changes in the 3D structure of a receptor induced by some effect, e.g., by binding of a ligand binding and/or by structural degradation, also can change the topography of solvent accessible chemical groups in the biomolecule, or both the topography and the type of the groups accessible to solvent. One result of these changes may be an alteration in the partition behavior of the biomolecule and/or the ligand-bound receptor, according to certain embodiments of the invention.

In some cases, the level of concentration of biomolecules in biological samples is dependent upon genotyping or reasons other than those related to the physiological condition under investigation. Thus, identification of differences in biomolecules attributable to diseased verses normal states may necessitate using a statistically significant number of samples to negate the effect of natural genetic or other variations in some embodiments of the invention. In some cases, the effect of genetic or other variability, leading to under- or overexpression, can be separated (e.g., fractionated) from differences to biomolecules that are traced to their diseased versus normal states. This separation can be achieved by subjecting a sample or other mixture of species containing biomolecules or other molecules to partitioning or separation in one or more different systems, and determining a comparative pattern of species in the sample/mixture with various components of the system(s), according to various embodiments. This can be accomplished, e.g., by separating and/or fractionating, using conventional techniques, the two interacting components of each sample, calculating the pattern of partition coefficients calculated for each species in the diseased and normal samples, and utilizing such pattern for further analysis. As specific non-limiting examples, obtaining a comparative pattern can involve fractionating or separating at least a portion of the first portion and second portion (and/or more portions) of the system. This fractionating or separation can involve techniques including electrophoresis such as one-dimensional electrophoresis, two-dimensional electrophoresis, liquid or other chromatography, direct or subsequent analysis performing mass spectrometry on at least a portion of the first, second (and, alternately, more portions) of the system, or the like, and in some cases, can involve a point-by-point basis of comparison. Other techniques include other spectrographic techniques (e.g., UV, visible, IR, Raman, etc.), etc. Different partition coefficients may not be related to the absolute level of expression of each species, but instead, may be related to changes to the structure, binding to other molecules or other changes of relevance to their biological effects, etc. Thus, the present invention provides, in one set of embodiments, methods for the identification of changes to biomolecules in a biological mixture that may be inherent in their structure and thus more closely to their function and not their absolute level, and in some cases without necessarily requiring a large statistical number of samples to negate the effect of individual variability in the expression levels.

The use of a pattern of partition coefficient values that is obtained from multiple systems (a "signature") can be used to enhance the specificity of certain methods of the invention. In yet other embodiments, partitioning of the samples in multiple systems and performing the steps above, then observing the pattern of values for one or more biomolecules, can provide another way to constructing a sensitive and specific diagnostics method.

In some embodiments, such changes may be detected using other systems and methods which have an underlying dependence upon the topography and/or the types of solvent accessible groups. Examples of such other methods include, but are not limited to, column liquid-liquid partition chromatography (LLPC), a heterogeneous two-phase system, a multiphase heterogeneous system, etc. In some cases, an apparent partition coefficient may be generated that expresses the relative changes in the average partitioning between a first and a second phase. For example, in LLPC, the retention volume of a receptor may be used as the apparent partition coefficient.

Aqueous two-phase systems are well-known to those of ordinary skill in the art and can arise in aqueous mixtures of different water-soluble polymers or a single polymer and a specific salt. When two or more certain polymers, e.g., dextran ("Dex") and polyethylene glycol ("PEG"), or one or more certain polymers and one or more inorganic salts, e.g. polyvinylpyrrolidone ("PVP") and sodium sulfate, are mixed in water above certain concentrations, the mixture can separate into two immiscible aqueous phases under certain conditions. There may be a discrete interfacial boundary separating two phases, for example, such that one is rich in one polymer and the other phase is rich in the other polymer or the inorganic salt. The aqueous solvent in one or both phases may provide a medium suitable for biological or other species. Two-phase systems can also be generalized to multiple phase system by using different chemical components, and aqueous systems with a dozen or more phases are known in the art and can be used in connection with the invention.

When a species is introduced into such a two-phase system, it may distribute between the two phases. In this and other systems (e.g., multiphase systems having three or more such phases), the species can be found at different concentrations within each phase, or can be at the same concentration within each phase. Partitioning of a solute can be characterized by the partition coefficient "K," defined as the ratio between the concentrations of the solute the two immiscible phases at equilibrium. It has previously been shown that phase separation in aqueous polymer systems may result from different effects of two polymers (or a single polymer and a salt) on the water structure (see, e.g., B. Zavlavsky, *Aqueous Two-Phase Partitioning: Physical Chemistry and Bioanalytical Applications*, Marcel Dekker, New York, 1995). As the result of the different effects on water structure, the solvent features of aqueous media in the coexisting phases can differ from one another. The difference between phases may be demonstrated by techniques such as dielectric, solvatochromic, potentiometric, partition measurements, or the like.

The basic rules of solute partitioning in aqueous two-phase systems have been shown to be similar to those in water-organic solvent systems (which can also be used as systems in the present invention). However, what differences do exist in the properties of the two phases in aqueous polymer systems are often very small, relative to those observed in water-organic solvent systems, as would be expected for a pair of solvents of the same (aqueous) nature. The small differences between the solvent features of the phases in aqueous two-phase or multi-phase systems can be modified so as to amplify the observed partitioning that results when certain structural features are present.

The polymer and/or salt compositions of each of the phases may depend upon the total polymer and/or salt composition of an aqueous two-phase system. The polymer and/or salt composition of a given phase, in turn, can govern the solvent features of the aqueous media in this phase. These features include, but are not limited to, dielectric properties, solvent polarity, ability of the solvent to participate in hydrophobic hydration interactions with a solute, ability of the solvent to participate in electrostatic interactions with a solute, and hydrogen bond acidity and basicity of the solvent. All these and other solvent features of aqueous media in the coexisting phases may be manipulated by selection of polymer and salt composition of an aqueous two-phase system. These solvent features of the media may govern the sensitivity of a given aqueous two-phase system toward a particular type of solvent accessible chemical groups in the receptor. This sensitivity, type, and topography of the solvent accessible groups in two different proteins, for example, can determine the possibility of separating proteins in a given aqueous two-phase system.

In some cases, a particularly sensitive system may be required, e.g., a system that is very sensitive to two very similar species, or a system able to detect differences in conformation of a single species, etc. This sensitivity may be of importance when, for example, subtle differences are being detected between the conformational changes in a receptor induced by binding of closely related chemical compounds. The present invention provides, in some embodiments, efficient and successful systems and methods for screening compositions to identify and/or amplify differences between the compositions of two mixtures. By utilizing a wide variety of different conditions to screen each molecule, as described herein, different partitioning or separation behavior may be obtained reliably, without the need to fully understand the underlying theory of aqueous two-phase partitioning, or any of the other related or substitutable separation techniques.

Biomolecules such as proteins, nucleic acids, etc. may be distributed between the two or more phases when placed into such a system. For example, in the case where phase-forming polymers are used, solutions comprising one or more of the two polymers and the biomolecule may be mixed together such that both phase-forming polymers and the biomolecule are mixed. The resulting solution is resolved and a two-phase system is formed. Optionally, centrifugation can be used to enhance separation of the phases. In yet another embodiment, the partitioning may be conduced in a microfluidic device, in which two liquid streams are brought into close contact in a narrow channel thus facilitating partitioning of species without requiring agitation and centrifugation. It will be recognized by those of ordinary skill in the art that partitioning behavior of a biomolecule may be influenced by many variables, such as the pH, the polymers used, the salts used, factors relating to the composition of the system, as well as other factors such as temperature, volume, etc. Optimization of these factors for desired effects can be accomplished by routine practice by those of ordinary skill in the relevant arts, in combination with the current disclosure.

Evaluation of data from partitioning of a biomolecule or other species can involve use of the partition coefficient(s), in some embodiments. For example, the partition coefficient of a protein can be taken as the ratio of the protein in first phase to that in the second phase in a biphasic system. When multiple phase systems are formed, there can be multiple independent partition coefficients, each of which can be defined between any two phases. It will be recognized that the partition coefficient for a given biomolecule or other species of a given conformation will be a constant if the conditions and the composition of the two-phase system to which it is subjected remain constant. Thus, for example, if changes are observed in the partition coefficient for a protein upon addition of a potential binding partner, these changes can be presumed to result from changes in the protein structure caused by formation of a protein-binding partner complex. The partition coefficient in such cases is a specifically mathematically defined quantity, and the term includes coefficients representing the relative measure of interaction between a species and at least two interacting components. It should also be recognized that differences between partition coefficients of corresponding species in two or more mixtures could indicate, in addition to potential structural changes, binding or lack of binding of such species to other species in the mixtures. The present invention makes specific use of patterns of partition coefficients and not necessarily their individual counterparts for purposes described herein.

In a non-limiting example of one partitioning system, aqueous multiphase systems are known to be formable from a variety of substances. For example, in order to determine the partition coefficient of a protein (or a mixture of a protein with another compound) to be analyzed, concentrated stock solutions of all the components (polymer 1, e.g., dextran; polymer 2, e.g., PEG, polyvinylpyrrolidone, salts, etc.) in water can be prepared separately. The stock solutions of phase polymers, salts, and the protein mixture can be mixed in the amounts and conditions (e.g., pH from about 3.0 to about 9.0, temperature from about 4° C. to 60° C., salt concentration from 0.001 mol/kg to 5 mol/kg) appropriate to bring the system to the desired composition and vigorously shaken. The system can then be allowed to equilibrate (resolution of the phases). Equilibration can be accomplished by allowing the solution to remain undisturbed, or it can be accelerated by centrifugation, e.g., for 2-30 minutes at about 1000 g to about 4000 g, or higher in some cases. Aliquots of each settled (resolved) phase can be withdrawn from the upper and/or lower phases (or from one or more phases, if multiple phases are present). The concentration of molecule(s) or other species can then be determined for each phase.

Different assay methods may be used to determine the relative measures of interaction between species and interacting components in various embodiments, e.g. in the form of the concentration of the biomolecules in each phase of a multi-phase system. The assays will often depend upon the identity and type of biomolecule or other species present. Examples of suitable assay techniques include, but are not limited to, spectroscopic, immunochemical, chemical, fluorescent, radiological, and enzymatic assays. When the biomolecule is a peptide or protein, the common peptide or protein detection techniques can be used. These include, but are not limited to, direct spectrophotometry (e.g., monitoring the absorbance at 280 nanometers) and dye binding reactions with Coomassie Blue G-250 or fluorescamine, o-phthaldialdehyde, or other dyes and/or reagents. Alternatively, if the protein is either an antibody or an antigen, certain immunochemical assays can be used in some cases. In the case of mass spectrometry, the peak height at a specific m/z spectral location may be proportional to the concentration of the specific protein in some instances, or the peak height at a specific elution time may be proportional to the same.

The concentration of the biomolecule(s) or other species in each phase, or in one phase and the original sample, can be used to determine the partition coefficient of the sample under the particular system conditions, in some embodiments of the invention. Since the partition coefficient reflects only the ratio of the two concentrations, the absolute values may not be required. It will be recognized that this can allow certain analytical procedures to be simplified, e.g., calibration can be eliminated in some instances. It also may have significant advantages for negating the effect of natural variability in the absolute concentration of proteins in samples obtained from, e.g., biological systems, when comparing two or more samples, thus focusing on those changes detected as differences in the partition coefficient relevant to changes to the structure of the individual species in the samples.

It should be recognized by those skilled in the art that the steps in above description of obtaining the partition coefficient could be substituted by others. Depending on the size, volumes, amount of the biomolecule, detection system, discrete or continuous operation using either liquid-liquid or liquid-solid partioning, chromatography, or other processes that effectively result in results described herein may be used. Such modifications and different processes do not limit the scope of the present invention.

The partition coefficient can also be compared with other partition coefficients, in some embodiments of the invention. For example, a partition coefficient for a species can be compared to the partition coefficients for the species under different conditions, a partition coefficient for a species can be compared to the partition coefficients for the species when combined with other species, a set of partition coefficients for a species can be compared to other sets of partition coefficients, etc. The pattern obtained from a series of partition coefficients, e.g., vs. m/z using mass spectrometry or elution time for HPLC or other chromatographic techniques, etc., can be compared to other patterns obtained under different conditions, etc. In the case of mass spectrometry analysis, the signal value at each m/z for, e.g., the top phase of a partitioning system may be divided by the signal value at the same m/z from the bottom phase of the same partitioning system in some cases to yield a value of the partition coefficient at the same specific m/z. As another non-limiting example, the absorbance values at each desired time in an HPLC chromatogram for the top phase may be divided by their counterpart bottom values corresponding to the same time to yield a chromatogram of the partition coefficients, in some instances. These spectra or chromatograms may also be referred to as patterns or data patterns in the present invention. This comparative information can be obtained, in some cases, at the same time or near the same time and in the same system or a similar system as is used to determine the interaction characteristics of the molecules of interest, or can be provided as pre-prepared data in the form of charts, tables, or electronically stored information (available on the Internet, disc, etc.).

In one embodiment of the present invention, proteins or other biomolecular mixtures from an experimental sample and from a reference sample (determined simultaneously, previously, or subsequently, as described above) may be caused to partition in a variety of different aqueous two-phase systems, e.g. formed by different types of polymers, such as Dextran and PEG or Dextran and Ficoll, by the same types of polymers with different molecular weights, such as Dextran-70 and PEG-600 or Dextran-70 and PEG-8,000, by the same polymers but containing different in type and/or concentration salt additives, different buffers of different pH and concentration, etc. In some cases, the overall partition coefficients for the mixtures determined using a particular assay procedure (same for both samples) can be determined in all of the systems. In one embodiment, the systems displaying different partition coefficients for the mixtures under comparison may be selected as a separation medium, for example, for further fractionation and/or characterization of the mixtures. In another embodiment, mixtures are partitioned or otherwise separated using one or more standard systems with known properties, e.g., those providing enhanced sensitivity levels towards hydrophobic or ionic interactions. In such cases, the pattern of individual partition coefficients of the species comprising the mixtures may be determined following separation of the mixtures in the phases and/or compared between two or more mixtures.

The reasons for the observed differences in the partition behavior of the two samples do not necessarily have to be scientifically characterized for such differences to be useful for many applications, e.g., for diagnostics. Such differences, resulting in partitioning behavior, may arise due to multiple reasons, including relative compositional, structural, or conformational differences in the samples when exposed to aqueous media of different solvent structures. Also, the identity of the species contained in the pattern of partition behavior of the two samples need not be known for the differences between the two patterns to be useful for certain applications.

In one set of embodiments, the systems and methods proposed herein provide techniques for the separation and fractionation of proteins while preserving complexes and biomolecular interactions that may be of interest to distinguishing among samples. The solvent media in aqueous partitioning may be selected to be compatible with the mixture of biomolecules. The solvent media may also be selected to preserve the higher-order structures, as well as non-covalent binding among biomolecules such as proteins, small molecular weight ligands, etc. For example, appearance or disappearance of complexes by the methods of this invention can be useful for diagnostics and other applications. As a consequence of such embodiments, the partition coefficients at any specific m/z or elution time may reflect the presence or absence of such biomolecular interactions.

One aspect of the present invention provides systems and methods able to distinguish among different samples, without being rigidly tied to few separation dimensions or variables, such as charge and/or size. One non-limiting example application of the present invention is to provide an adjustable separation dimension, in which changes to the pattern of individual species can be uncovered via determination of their pattern of individual partition coefficients or data patterns, enabling detection and identification of changes that cannot be detected using conventional separation means, such as molecular size or charge, and in which the absolute levels of concentration of such individual species is not reflected in the pattern itself.

One embodiment of the present invention provides systems and methods for discovering a pattern of biomolecules in a biological sample, which, in some cases, may be changed between normal and diseased state of the underlying organism. In some cases, a set of typically multiple systems, each known to provide sensitivity to structural changes leading to differences in their hydrophobic, ionic, etc. interactions with the interacting components, can be tested with the same samples. One or more patterns can be identified as markers in one or more systems using techniques described herein, in certain embodiments. This marker or markers can also subsequently be used for diagnostics applications.

In yet another embodiment, a set of markers and the associated systems in which such markers were discovered can be used for diagnostics screening. For example, the diagnostics test can include one or more of the following steps which can be carried out in any order suitable for such screening: (1) Partitioning or otherwise separating the sample in one or more of the systems which were used during the marker discovery study; (2) Processing the partitioned sample to obtain two or more patterns of species concentration vs. m/z or elution time; (3) From each two corresponding patterns, calculating the comparative pattern of partition coefficients vs. m/z or elution time; (4) Comparing the comparative patterns to those representing normal and diseased states which were obtained during the marker discovery study using any combination of statistical or mathematical techniques; and (5) Denoting a diagnostics based on such a comparison, alone or in conjunction with other information.

As a specific non-limiting example, without loss of generality, comparing patterns of data obtained form at least two phases of a partitioning system, or from one phase and the original system, may result in at last two typical cases. In some cases, at the same (or practically the same) ordinate parameter used to describe the pattern, e.g., a specific m/z value or elution time, two finite values of the measured physical property (e.g., concentration) may be found in the two phases. In some cases, a partition coefficient specific to the ordinate location can be mathematically defined as the ratio of such properties.

In other cases, at the same (or practically the same) ordinate location, the sample from one of the phases may display a finite value of the measured physical property while the other does not. Such a case may mean that the individual species corresponding to that ordinate location was totally or practically totally separated into one of the phases. In certain instances, the partition coefficient specific to the ordinate location can be mathematically described as zero, infinity, or other categorical rather than numerical values.

As a specific, non-limiting example of the first case, a pattern of the measured property and the processed pattern of partition coefficients may be as follows:

|  | m/z | | | | | |
| --- | --- | --- | --- | --- | --- | --- |
|  | 350 | 400 | 1100 | 12000 | 13500 | 17000 |
| Top phase peak | 3000 | 4000 | 1000 | 5000 | 14000 | 28000 |
| Bottom phase peak | 1000 | 2000 | 2000 | 7500 | 14000 | 100000 |
| Partition Coefficient | 3 | 2 | 0.5 | 0.714 | 1 | 0.28 |

As a specific, non-limiting example of the second case, a pattern of the measured property and the processed pattern of partition coefficients may be as follows:

|  | m/z | | | | | |
| --- | --- | --- | --- | --- | --- | --- |
|  | 100 | 450 | 1500 | 11000 | 11500 | 18000 |
| Top phase peak | 3000 | 0 | 0 | 5000 | 14000 | 0 |
| Bottom phase peak | 0 | 2000 | 2000 | 0 | 0 | 1000 |
| Partition Coefficient | INF | ZERO | ZERO | INF | INF | ZERO |

Without loss of generality, these patterns could be described by the following four cases, according to such embodiments:
1. A pattern of partition coefficients vs. an ordinate location.
2. A pattern of difference of the property values at specific ordinate location vs. the ordinate location.
3. A pattern of categorical values corresponding to zero or infinity partition coefficient values vs. an ordinate location.
4. A mix of any of the above cases. In such a case, a pattern is comprised of a series of numbers and categorical values vs. the ordinate value, together with a corresponding series of symbolic designators at the same ordinate values that provides for annotation of the meaning of the specific entry in the pattern.

As another non-limiting example, a pattern may be described as:

|  | m/z | | | | | |
| --- | --- | --- | --- | --- | --- | --- |
|  | 1000 | 4500 | 15000 | 19000 | 20000 | 21000 |
| Partition Coefficient | INF | 0.35 | ZERO | 5.1 | INF | 1.15 |

Without a loss of generality, searching for a biomarker or a set of biomarkers (e.g., to increase clinical specificity), according to some embodiments, and denoting a disease can involve one or more of the following steps, carried out in any suitable order:
1. Preparing one or more aqueous two-phase partitioning systems.
2. Adding samples of plasma (homogenized tissue, urine, saliva, etc.) corresponding to normal and diseased state origins.
3. Partitioning the samples in the aqueous two-phase systems.
4. Removing aliquots from both phases of the aqueous two-phase systems (or from one phase and the original sample) for each sample. After this step there will be two aliquots for each sample.
5. Optionally, performing additional separation steps (e.g., HPLC or absorbance to solid support favoring certain classes of proteins) to separate groups of proteins in each aliquot according to a specific physical property, e.g., size or charge.
6. Generating a mass spectra pattern of the sample in each aliquot using mass spectrometer vs. its m/z value.
7. Calculating the ratio of the point-by-point corresponding spectral data in each set of aliquots from the same sample, using categorical values to denote absence of the property value at certain m/z value in either of the two phases.
8. Using mathematical or statistical techniques, comparing the comparative patterns of the ratios and/or categorical values for the normal vs. diseased states.
9. Selecting one or more patterns, together with the partitioning systems and other separation steps used to define such patterns, as potential biomarker by their designation as different using the mathematical or statistical techniques for the two types of samples.

It should be noted that discovering and selecting the marker(s), as discussed above, does not necessarily require the protein to be identified. In some cases, the marker may comprise a pattern of species selected in the manner described herein. In one embodiment, the specific composition of the aqueous two-phase partitioning system or other system may be used to determine the ratio as being the partition coefficients. Multiple partitioning systems of different compositions can also be used in methods similar to the ones described above. The selection of a set of markers for subsequent diagnostics may also depend on factors such as the competing attributes of the increase in specificity, costs when additional biomarkers are included in the final set, or the like.

Once a set of biomarkers is discovered using techniques similar to those described above, a diagnostics screening test can be devised, according to some embodiments of the invention. As a non-limiting example, without loss of generality, a test may be conducted as follows:

1. Obtain a sample of plasma (homogenized tissue, urine, saliva, etc.) corresponding to unknown state (normal or diseased).
2. Add aliquots of the sample to the partitioning system used during the discovery of the biomarkers. If more than one system was used, repeat the same step for each different partitioning system.
3. Perform partitioning of the sample in each of the systems.
4. Perform any additional separation steps in accordance with the steps used to define and select the patterns that correspond to the different states of the samples.
4. Obtain the mass spectrum of each of the partitioned phases.
5. Calculate the pattern of partition coefficients for each of the partitioned phases (use categorical values as necessary as described above).
6. Compare, using appropriate mathematical or statistical techniques the comparative pattern comprised of partition coefficients and/or categorical values from the sample of unknown origin to those corresponding to the normal and diseased states.
7. Classify the unknown sample as diagnostically similar to one of the known samples.

In some embodiments, the biomarker may represent a mixture of forms of the same protein, and/or mixtures which complex between biomolecules or between biomolecules and other molecules that may appear or disappear between normal and diseased states. Changes in the distribution or relative amounts of the different forms of the same protein may result, in some cases, in a different partitioning behavior of the same protein, and appearance or disappearance of complexes may result in the appearance or disappearance of, e.g., spectral peaks.

Some aspects of the invention provide a variety of studies, at the level of determining tools for physiological analysis and/or for carrying out physiological analysis. For example, tools for determining analysis procedures can involve taking samples from a single individual or multiple individuals. In one embodiment, a positive sample and a control sample can be taken from a single individual. For example, an individual may have a tumor and a positive sample may be a portion of the tumor, where a control sample is from a non-tumorous portion of the individual. The samples, both positive and control, can be taken from the individual at the same time or at different times. For example, samples from a tumorous portion of an organism can be taken at different times, and used to determine differences in the patterns of the samples as tools for analysis of the progression of a tumor.

In some cases, single patterns or multiple patterns can be used as markers. Multiple patterns from a single sample can be identified as separate markers for a particular condition, and during analysis, separate patterns can be studied in certain instances. As one example, a single pattern can define a marker identified by and/or studied in connection with a single partitioning system. In another embodiment, multiple patterns from a single sample can be identified as separate markers for a particular condition using multiple partitioning systems, and during analysis separate patterns can be studied.

The analytical tool used to evaluate the pattern of partition coefficients or the categorical values may be, e.g., a mass spectrometer, liquid chromatography such as HPLC, or other spectral techniques such as UV, IR, Raman or other absorbance and/or scattering techniques. The ordinate for the pattern in each case depends on the technique, for example, m/z for mass spectra, time for HPLC, wavelength for most spectral techniques, etc. The technical aspects of the method may result in a pattern of one or more peaks (e.g., values at specific m/z) or a diffuse pattern obtained as a summation of responses from many molecules at each specific wavelength (e.g., an HPLC chromatogram or UV-Vis absorbance spectrum). The mathematical techniques used to analyze such patterns may vary depending on the technique used, as is understood by those of ordinary skill in the art, and the relative choice of each analytical tool will be determined primarily by its sensitivity, resolution, and other operational characteristics without a loss of generality of the present invention.

Mathematical and statistical pattern recognition techniques may be used, in some cases, to analyze the data, including linear and non-linear techniques, such as principal component analysis, partial least squares, artificial neural networks, genetic algorithms, Fourier or wavelet transforms, etc. One or more such algorithms may be used to process, transform, condense, or manipulate the series of partition coefficient and/or categorical values, in some cases. The raw values or their processed data corresponding to a given mixture of species (e.g., serum sample from a positive case) may be compared using such techniques to similarly obtained and processed data corresponding to a different mixture of species (e.g., from a negative case). During pattern discovery, such techniques may be provided with multiple examples of samples of different classes and analytical discriminatory aspects of the data are discovered and presented in mathematical or statistical manner. In certain instances, such techniques may make use the discriminatory aspects previously discovered to interrogate new data obtained from similarly conducted experiments and subsequently critically compare such data to previously known cases for identification.

According to one aspect of the present invention, a computer and/or an automated system is provided able to automatically and/or repetitively perform any of the methods described herein. As used herein, "automated" devices refer to devices that are able to operate without human direction, i.e., an automated device can perform a function during a period of time after any human has finished taking any action to promote the function, e.g. by entering instructions into a computer. Typically, automated equipment can perform repetitive functions after this point in time. One specific non-limiting example of a technique that can make use of a computer or other automated system is in a process in which a physiological condition of a system as determined by determining a relative measure of interaction between one or more species from a sample from the system and various interacting components of a partitioning system. In the clinical setting, this may be accomplished, for instance, by drawing a sample of blood (milliliter-sized or a very small sample such as a drop or less) and subjecting the blood sample or a subset thereof (e.g., plasma) to a multi-phase partitioning process. The results of this process can then be compared to similar behavior of markers in a similar system, which can take the form of data stored electronically.

FIG. 1 is a schematic block diagram of an example system according to one embodiment of the present invention. In the embodiment illustrated in FIG. 1, a controller 200 is implemented on a conventional personal computer 250 that includes a processor 251, a memory 252, an input device 253, optionally a removable storage device 254, a pointing device 255, a display device 256, and a communication device 257, all coupled together via a bus 258. In a conventional manner, memory 252 may include a variety of memory devices, such as hard disk drives or optical disk drives, RAM, ROM, or other memory devices and combinations thereof, and input device 253 may include a keyboard, a microphone, or any other form of input device capable of receiving one or more inputs 210 from a user of controller 200. Removable storage device 254 may include a CD-ROM drive, a tape drive, a diskette drive, etc. and may be used to load application software, including software to implement various embodiments of the present invention described herein. Display 256 may include a conventional CRT display screen, a flat panel display screen, or any other type of display device that allows textual information to be displayed to the user, and pointing device 255 may include a puck, a joystick, a trackball, a mouse, or any other type of pointing device or scrolling device that permits the user to select from among the various textual information displayed on the display device 256. Communication device 257 may include any form of communication transceiver capable of receiving one or more inputs 220 from the fluid-handling apparatus 30 and providing one or more outputs to the fluid-handling apparatus 30. For example, communication device 257 may include a RS232/485 communication transceiver, a 4-20 mA analog transceiver, an Ethernet transceiver, etc.

Software, including code that implements embodiments of the present invention, may be stored on some type of removable storage media such as a CD-ROM, tape, or diskette, or other computer readable medium appropriate for the implemented memory 252 and the removable storage device 254. The software can be copied to a permanent form of storage media on the computer 250 (e.g., a hard disk) to preserve the removable storage media for back-up purposes. It should be appreciated that in use, the software is generally and at least partially stored in RAM, and is executed on the processor 251.

Various embodiments of the present invention can also be implemented exclusively in hardware, or in a combination of software and hardware. For example, in one embodiment, rather than a conventional personal computer, a Programmable Logic Controller (PLC) is used. As known to those skilled in the art, PLCs are frequently used in a variety of process control applications where the expense of a general purpose computer is unnecessary. PLCs may be configured in a known manner to execute one or a variety of control programs, and are capable of receiving inputs from a user or another device and/or providing outputs to a user or another device, in a manner similar to that of a personal computer. Accordingly, although embodiments of the present invention are described in terms of a general purpose computer, it should be appreciated that the use of a general purpose computer is exemplary only, as other configurations may be used.

As shown in FIG. 1, the controller 200 is adapted to be coupled to a fluid handling apparatus 30, to control operation of the fluid handling apparatus. Controller 200 includes an input 210 to receive one or more parameters from a user of the controller 200 relating to the desired operation to be performed. The controller 200 also includes a plurality of inputs 220 to receive signals relating to the operational status of the fluid handling apparatus, and a plurality of outputs 230, 240 to configure and control the fluid handling apparatus. User input parameters received on input 210 may include the type and amount of protein and/or other biomolecules that is to be processed by the fluid handling apparatus, the compositions of liquids used by the fluid handling apparatus for, e.g., liquid-liquid partitioning, etc.

Some embodiments of the present invention permit the user to specify one or a number of input parameters relating to the operation of the fluid handling apparatus, and then, based upon the input parameters, to configure and control the fluid handling apparatus. Depending upon the number of input parameters specified by the user, the controller may prompt the user for additional parameters prior to configuring the fluid handling apparatus.

Inputs 220 of controller 200 are adapted to receive a plurality of signals relating to the operational status of the fluid handling apparatus. Signals that may be received on inputs 220 generally correspond to physical conditions within the fluid handling apparatus, and may include, for example, the concentration of proteins or other molecules within the fluid handling apparatus, the time of exposure, the time for settling to occur, the degree of agitation, the operating temperature or pressure, etc.

Outputs 230, 240 of the controller 200 are adapted to configure and control the fluid handling apparatus, based upon the user parameters received at input 210, and optionally, one or more of the signals received on inputs 220. Output 230 may provide a number of separate signals, for example, a signal to introduce a protein or other molecule within a liquid, a signal to control the operating temperature, etc.

According to another embodiment of the present invention, controller 200 may include a database and/or a knowledgebase that can be accessed by processor 251. According to one embodiment of the present invention, the database may include a plurality of records, each record corresponding to a particular set of parameters for which the fluid processing apparatus may be used to determine a relative measure of interaction. Unless specifically indicated otherwise, as used hereinafter, the term "parameters" is used to refer to both process parameters (e.g., the amount of protein or other biomolecule(s) to be added, the operating temperature etc.), as well as characteristics (e.g., concentration, separation time, etc.) of the experiment given a particular set of process parameters. In general, each of the records stored in the database reflects empirical data based upon use of the fluid processing apparatus under defined conditions, or the use of a similar fluid processing apparatus under defined conditions. The controller 200 and the database may thus be viewed as forming an "expert" system. The database may be stored on a removable storage medium and copied to memory 252 for use by the processor 251, or alternatively, the controller may be pre-configured to include the database.

In some cases, the database (or knowledgebase) may be configured for a particular type of fluid handling apparatus (e.g., a specific model from a particular manufacturer of fluid handling apparatus), or may be configured to be used with a variety of types of fluid handling apparatuses. In some cases, the database may be configured for a particular type of protein and/or other biomolecule. Alternatively, a more general database may be used that includes a number of different proteins, biomolecules, aqueous solutions, etc. with which a variety of different fluid handling apparatuses may be used. In use, the database may be accessed by a fluid handling apparatus configuration and control routine that is performed by controller 200 to configure and control fluid handling apparatus 30 that is operatively coupled thereto. It should be appreciated that while the database or knowledgebase is initially based on empirical data obtained with similar equipment, the database may be periodically updated (e.g., new records may be added and/or existing records may be modified) to reflect additional data obtained in use, or by use of similar equipment. Another aspect of the database is related to its capacity for storage and retrieval of pattern information related to raw or processed data from the analysis instrumentation. Such data might include sequence of values, categorical information, mathematical coefficients, and other method-specific and sample-specific information useful for discovery and use of such patterns for the applications described herein.

The techniques and apparatus described herein can be used to discover markers or to execute a diagnostics test. The apparatus could be interfaced to other devices and instruments known to those skilled in the art, including automated sample preparation instruments, liquid chromatography columns, HPLC systems, mass spectrometers, absorbance instruments, etc. Data obtained from such devices and instruments could be electronically channeled to a software for performing data reduction and analysis and for delineating a diagnostics.

The following examples illustrate the analysis of patterns obtained from different experimental data for diagnosis applications. These examples are intended to illustrate certain embodiments of the present invention, but not exemplify the full scope of the invention.

Example 1

Using 2D-HPLC Data to Discover Patterns in Elution Profiles that, when Considered Together with their Diagnosis, May Provide Means to Determine the Latter in Unknown Samples This example is provided to illustrate the use of an embodiment of the invention for diagnosis purposes, and describes one technique provided by the present invention and a methodology for analyzing a medical condition, but is not intended to provide a specific marker or identifier for a specific medical condition.

Blood samples containing 4.5 mL were drawn from healthy donors (control) and patients with post-traumatic stress disorder (PTSD). The blood samples were collected into glass BD Vacutainer tubes containing 0.5 mL 3.2% sodium citrate and centrifuged at 1,000 rpm for 45 min at 8° C. The plasma was carefully removed, aliquoted and frozen at −80° C. The samples were thawed and subjected to partitioning in a aqueous poly(ethylene glycol)-sodium sulfate-Na/K-phosphate buffer, pH 7.4 two-phase system.

The aqueous two-phase system used in these experiments contained 15.70 wt.% polyethylene glycol-600 (with a molecular weight of about 600), 9.47 wt.% sodium sulfate, and 2.30 wt.% Na/K-phosphate buffer, pH 7.4. The systems were prepared by mixing the appropriate amounts of stock polymer, salt, and buffer solutions by weight into a 100×75 mm tube up to a total weight of a system of 4.00 g. The ratio between the volumes of the two phases of each system (volume of the top phase to volume of the bottom phase) was about 1:1. A fixed amount of 600 microliters of blood plasma was added to a system. The system was vigorously shaken and centrifuged for 30 min at about 3500 rpm in a centrifuge with a bucket rotor to speed the phase settling. The tubes were taken out of the centrifuge, and samples from the top and the bottom phases were withdrawn. Aliquots containing about 0.3 ml from the top phase and 1.7 ml from the bottom phase were withdrawn, and each aliquot was diluted with starting buffer (Beckman-Coulter, Fullerton, Calif., USA) to 2.50 mL total volume. Each sample was vortexed and subjected to buffer exchange using PD-10 column (Amersham Pharmacia Biotech) as follows. The PD-10 column was equilibrated with 25 mL of start buffer. Each sample (2.5 mL) was loaded onto a PD-10 column, the column was washed with start buffer, and the first 2.5 mL fraction was collected.

A ProteomeLab PF 2D system from Beckman-Coulter (Fullerton, Calif.) was used for the 2D-HPLC analysis. Following the above procedure, a sample of 2.00 mL was injected, and first dimension separation was performed using a standard procedure with a flow rate of 0.2 mL/min, and by monitoring of the absorbance of the column effluent at 280 nm. During the pH gradient portion of the run extending from 8.0 to 4.0 pH, fractions at 0.3-pH intervals were collected as detected by a pH monitor, which controlled the fraction collector. Each collected fraction was subjected to second dimension separation by Reverse-Phase HPLC (RP-HPLC) using standard protocols from the manufacturer. The RP-HPLC experiments using 200 microliters volume of each fraction injected was performed at 50° C. with a flow rate of 0.75 mL/min, and absorbance of the column effluent was monitored at 214 nm.

Figure 3:
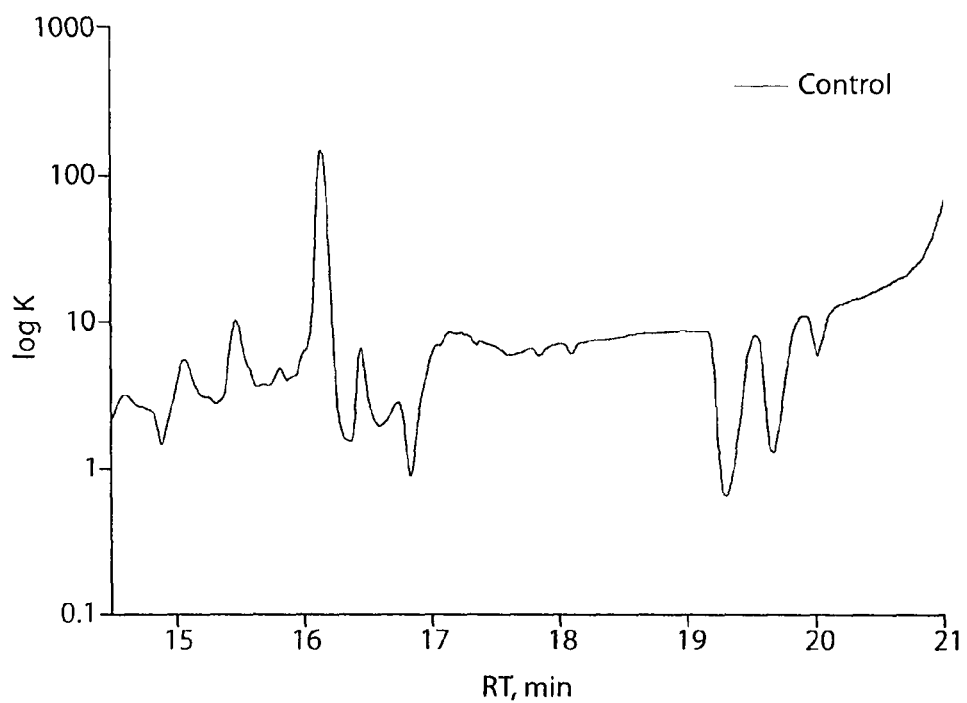
FIG. 3 is a comparative spectrum, derived from comparison of 2D-HPLC chromatograms of aliquots from different phases of a two-phase partitioning system after fractionation of a healthy (control) plasma sample.
Figure 4:
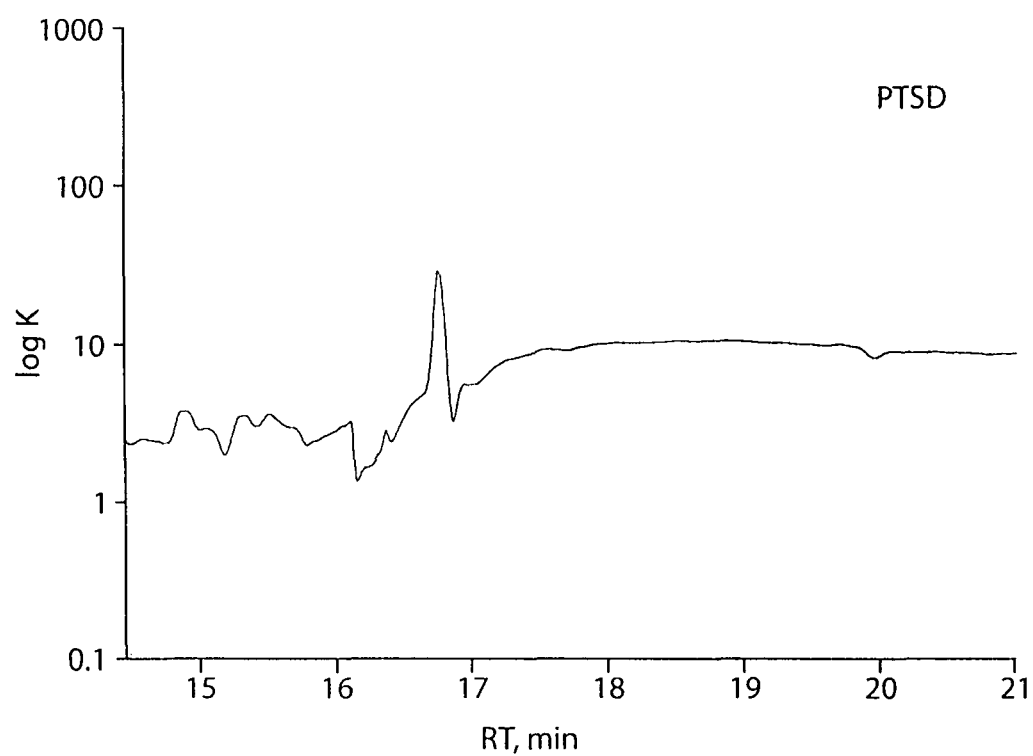
FIG. 4 is a comparative spectrum derived as that of FIG. 3, but from a patient previously diagnosed with posttraumatic stress disorder.

Chromatograms obtained under second dimension RP-HPLC for the corresponding plasma fractions (collected for the same pH intervals) from the samples obtained from the top and bottom phases were digitally stored on a system computer. Chromatograms of samples from healthy donors and from PTSD patients were compared after the second separation dimension at fixed pH intervals. In each case, a comparative spectrum (herein, a comparative chromatogram) of the point-by-point partition coefficients was constructed by dividing the data obtained from the top and the bottom of each sample. Additional mathematical operations to shift, smooth, clip, or transform any data pattern are totally arbitrary, as long as they are performed in the same manner on each sample. The comparative spectrum originating from a healthy donor (control) is shown in FIG. 3, and the corresponding comparative spectrum from a PTSD patient is shown in FIG. 4, both obtained from fractions having a pH range of 6.0 and 6.4. The two comparative spectra are visually different. Further mathematical and statistical techniques to compare the degree of similarity between the two spectra could readily be performed using automated procedures to classify additional samples of unknown diagnosis as similar to either of the samples analyzed herein. Such techniques could be used to arrive at a diagnosis using such a comparison, or more typically, in conjunction with other data and information. It should be noted that in some applications, many samples belonging to both negative and positive states of a diagnosis will be processed and combined by techniques known to those skilled in the art to define diagnosis tools that are statistically valid with respect to sensitivity and specificity levels.

Example 2

Patterns of Mass Spectra Could be Used to Analyze Serum Samples Obtained from Healthy and Ovarian Cancer Patients This example is provided to illustrate the use of an embodiment of the invention for diagnosis purposes, and describes one technique provided by the present invention and a methodology for analyzing a medical condition, but is not intended to provide a specific marker or identifier for a specific medical condition.

Pooled serum samples from healthy (sample identifier 0651) and ovarian cancer patients (sample identifier 4850) were obtained from the Clinical Proteomics Reference Laboratory (Gaithersburgh, Md.). The aqueous two-phase system used in these experiments contained 15.70 wt. % polyethylene glycol-600 (with a molecular weight of about 600), 9.5 wt. % sodium sulfate, 4.8 wt. % NaCl, and 0.64 wt. % Na/K-phosphate buffer, pH 7.4. Several such systems were prepared by mixing the appropriate amounts of stock polymer, salt, and buffer solutions by weight into microtubes up to a total weight of each system of 0.425 g. The ratio between the volumes of the two phases of each system (volume of the top phase to volume of the bottom phase) was about 1:1. A fixed amount of 75 microliters of blood serum was added to a system. The system was vigorously shaken and centrifuged for 30 min at about 3500 rpm in a centrifuge with a bucket rotor to speed the phase settling. The microtubes were taken out of the centrifuge, and samples from the top and the bottom phases were withdrawn. Aliquots of 60 microliters from the top phase and 60 microliters from the bottom phase were withdrawn and dispensed into separate microtubes followed by addition of 240 microliters of water into each microtube.

The aliquots were sent for mass spectra analysis at the Clinical Proteomics Reference Laboratory using Surface Enhanced Laser Desorption Ionization mass spectrometer (Ciphergen, Fremont, Calif.) according to the following protocol: (1) a Q10 chip (Ciphergen) was twice treated with phosphate buffer for 5 minutes; (2) each aliquot was added to each well of the chip and incubated for 60 minutes at room temperature; (3) the chip was washed three times with 150 microliters of phosphate buffer using 10 mixing cycles, followed by a single wash with water; (4) The chip was air dried for 10 minutes; (5) 1 microliter of SPA matrix in 50% acetonitrile/water with 0.5% TFA was added to the chip, which was then air dried for 15 minutes; (6) step (5) was repeated. The chip was then placed into the mass spectrometer. The above protocol was repeated once for each sample (two repeats in total).

Raw spectral intensity data and the total ion current for each sample were sent back to ANALIZA, Inc. (Cleveland, Ohio) for further analysis. Each spectral data vector, having pairs of mass over charge (m/z) and intensity values, was normalized with respect to its total ion current, then averaged with a second vector corresponding to the second repeat of the same sample. The averaged spectral data vectors of the top and bottom aqueous phases corresponding to the same sample were divided on a point-by-point m/z basis, resulting in a data vector of the relative measure of interaction, K, versus m/z. This protocol was repeated for both healthy and cancer pool samples.

Figure 5:
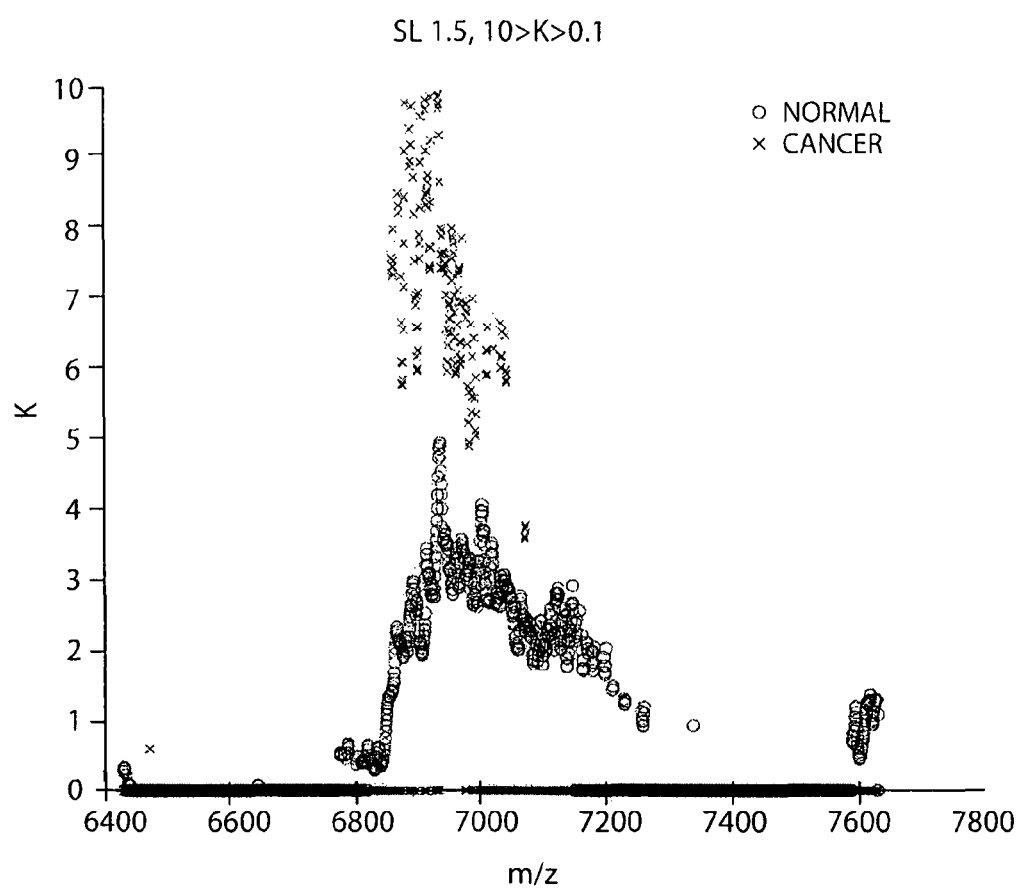
FIG. 5 shows a comparison of spectral K vectors for two samples, according to one embodiment of the invention.

A comparison of the spectral K vector for the two samples is shown in FIG. 5, for a selected range of m/z values. Consistent differences over a range of m/z between the cancer and the normal pooled samples may indicate a potential biomarker for early screening and/or other diagnostics applications.

Patterns of the relative measure of interaction vs. m/z can be developed from such data and subsequently used for diagnostics applications using techniques known in the art. Specific biomarkers could also be identified using mass spectrometry and other techniques and subsequently used to develop direct assays for measuring the relative measure of interaction specific to a biomarker using immunoassay and other techniques known in the art.

Figure 6:
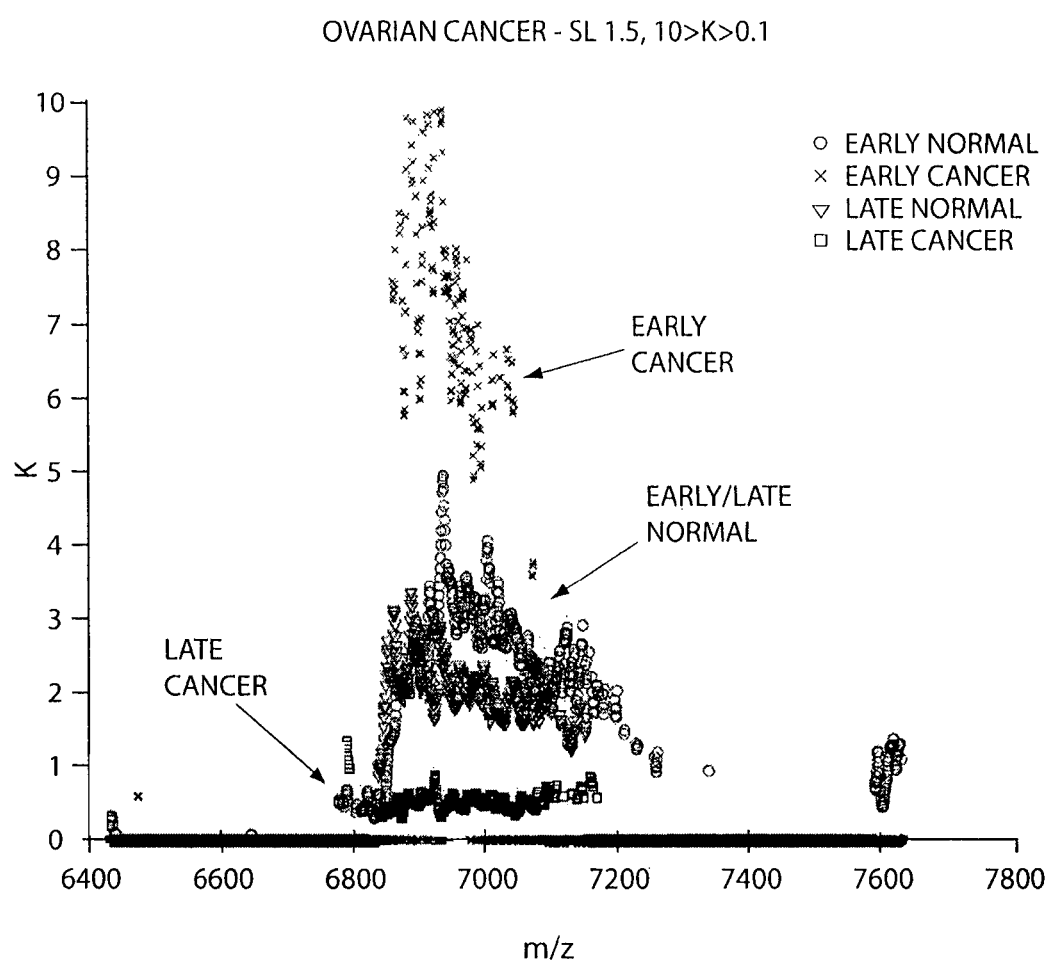
FIG. 6 illustrates certain biomarkers useful for distinguishing between early and late stage ovarian cancer, according to another embodiment of the invention.

Biomarkers developed using techniques described in the present invention can also be used to distinguish between early and later stage ovarian cancer, as illustrated in FIG. 6. The experimental protocol used was identical to the protocol described herein in Example 2. The two normal samples included different pools and exhibited certain variability. However, the variability between the two normal samples is significantly less than that between the early and late cancer samples. Other uses of biomarkers described in the present inventions could be developed for different applications.

Example 3

Patterns of Mass Spectra Discovered Using Present Invention Could have Certain Advantages Over Expression-Based Spectra This example is provided to illustrate the use of an embodiment of the invention for diagnosis purposes, and describes one technique provided by the present invention and a methodology for analyzing a medical condition, but is not intended to provide a specific marker or identifier for a specific medical condition. This example further illustrate a certain advantage of biomarkers that are discovered using techniques of the present invention over biomarkers that are discovered using conventional protein expression proteomics techniques.

Figure 7:
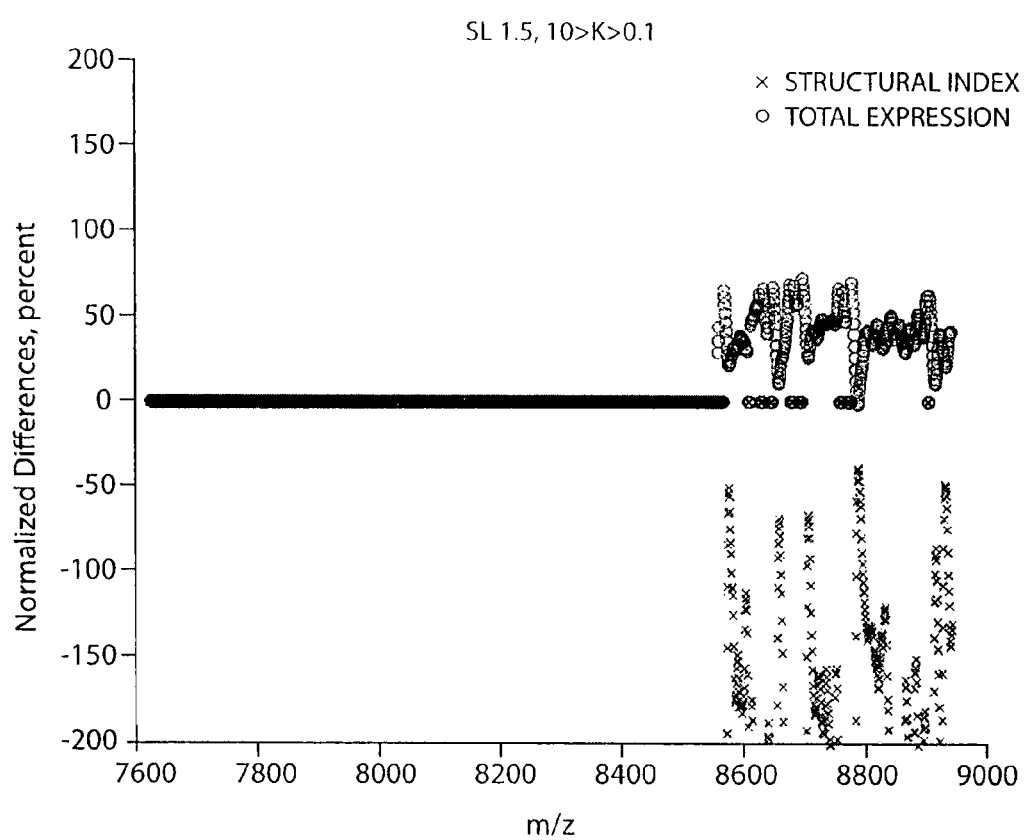
FIG. 7 shows data illustrating differences between normal and cancer subjects for a relative measure of interaction, in yet another embodiment of the invention.

Experimental techniques used in the present example are more fully described in Example 2, but with an aqueous two-phase system of different composition. An aqueous two-phase system contained 18.0 wt. % Ficoll-70 (with a molecular weight of about 70,000), 13.0 wt. % Dextran-75 (with molecular weight of about 75,000), 0.15 M NaCl, and 0.01 M Na/K-phosphate buffer, pH 7.4. Normalized differences defined as 100 (normal value−cancer value)/normal value were calculated from the data for the relative measure of interaction as described herein for the total protein expression. The data in FIG. 7 illustrates that the normalized differences between normal and cancer for the relative measure of interaction were significantly more distinct than those obtained using protein expression at the same m/z values. This observation is important for practical reasons, since it is well recognized that the natural variability of expression, which is not related to the underlying disease process, is a major hindrance in the discovery and the clinical use of expression level biomarkers, including m/z patterns of the same. In practice, differences of 50% in expression levels are sometime well within the natural variability bound and expression patterns as illustrated in FIG. 7. The same samples, when analyzed using the relative measure of interaction and its m/z pattern, have resulted in significantly more distinct differences between normal and cancer samples, which could be used to delineate the clinical origin of an unknown sample by its similarity to the pattern shown herein.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of", when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of determining at least one characteristic of a plurality of species, comprising:
    exposing a plurality of species to an aqueous partitioning system including at least first and second phases;
    obtaining, using mass spectroscopy, a first spectral data pattern comprising cumulative spectral information from a first sample of one or more species associated with the first phase of the aqueous partitioning system;
    obtaining, using mass spectroscopy, a second spectral data pattern from one or more of the following: (1) a second sample of one or more species associated with the second phase of the aqueous partitioning system, or (2) a portion of the plurality of species prior to the exposing step;
    constructing, on a computer, a comparative spectrum using mathematical operations using at least a portion of the first spectral data pattern and at least a portion of the second spectral data pattern, wherein at least some data points from the first spectral data pattern and at least some corresponding data points from the second spectral data pattern are combined together using mathematical operations comprising subtraction, division, and/or multiplication to produce data at least partially defining the comparative spectrum; and
    determining at least one characteristic of a plurality of species using the comparative spectrum.

2. The method of claim 1, comprising performing the method without determining the identity of at least one of the species in the plurality of species after exposing the at least one species to the aqueous partitioning system.

3. The method of claim 1, comprising performing the method without determining the level, abundance, concentration, and/or identity of any of the plurality of species after exposing the plurality of species to the aqueous partitioning system.

4. The method of claim 1, comprising performing the method without using information related to the level, abundance, concentration, and/or identity of any of the plurality of species after exposing the plurality of species to the aqueous partitioning system.

5. The method of claim 1, comprising performing the method without determining the identity of at least one of the species in the plurality of species prior to exposing the at least one species to the aqueous partitioning system.

6. The method of claim 1, comprising performing the method without determining the level, abundance, concentration, and/or identity of any of the plurality of species prior to exposing the plurality of species to the aqueous partitioning system.

7. The method of claim 1, comprising performing the method without using information related to the level, abundance, concentration, and/or identity of any of the plurality of species prior to exposing the aqueous partitioning system.

8. The method of claim 1, comprising performing the method without determining the identity of at least one of the species in the plurality of species prior to or after exposing the at least one species to the aqueous partitioning system.

9. The method of claim 1, comprising performing the method without determining the level, abundance, concentration, and/or identity of any of the plurality of species prior to or after exposing the plurality of species to the aqueous partitioning system.

10. The method of claim 1, comprising performing the method without using information related to the level, abundance, concentration, and/or identity of any of the plurality of species prior to or after exposing the plurality of species to the aqueous partitioning system.

11. The method of claim 1, comprising:
comparing the first spectral data pattern and the second spectral data pattern to define a comparative pattern; and
comparing the comparative pattern to a reference pattern to determine the at least one characteristic.

12. The method of claim 1, wherein the plurality of species is first fractionated prior to the act of exposing the plurality of species to the aqueous partitioning system.

13. The method of claim 1, wherein the first and second data patterns are compared without determining partition coefficients of a species of the plurality of species between the first and second phases.

14. The method of claim 1, wherein the plurality of species partitions between the first and second phases on the basis of structural differences.

15. The method of claim 1, comprising comparing at least a portion of the first spectral data pattern with at least a portion of the second spectral data pattern to determine a condition of a biological system.

16. The method of claim 1, wherein the second data pattern is representative of a sample indicative of an unknown condition of an organism.

17. The method of claim 1, wherein the method is performed without determining the chemical or biological identity of any of the plurality of species.

18. A method of determining at least one characteristic of a plurality of species, comprising:
exposing a plurality of species to an aqueous partitioning system including at least first and second phases;
obtaining a first data pattern comprising cumulative information from a first sample of one or more species associated with the first phase of the aqueous partitioning system;
obtaining a second data pattern comprising cumulative information by treating one or more of the following: (1) a second sample of one or more species associated with the second phase of the aqueous partitioning system, or (2) a portion of the plurality of species prior to the exposing step;
constructing, on a computer, a comparative spectrum using mathematical operations using at least a portion of the first data pattern and at least a portion of the second data pattern, wherein at least some data points from the first data pattern and at least some corresponding data points from the second data pattern are combined together using mathematical operations comprising subtraction, division, and/or multiplication to produce data at least partially defining the comparative spectrum; and
determining at least one characteristic of a plurality of species using the comparative spectrum.

19. The method of claim 18, comprising performing the method without determining the identity of at least one of the species in the plurality of species after exposing the at least one species to the aqueous partitioning system.

20. The method of claim 18, comprising performing the method without determining the level, abundance, concentration, and/or identity of any of the plurality of species after exposing the plurality of species to the aqueous partitioning system.

21. The method of claim 18, comprising performing the method without using information related to the level, abundance, concentration, and/or identity of any of the plurality of species after exposing the plurality of species to the aqueous partitioning system.

22. The method of claim 18, comprising performing the method without determining the identity of at least one of the species in the plurality of species prior to exposing the at least one species to the aqueous partitioning system.

23. The method of claim 18, comprising performing the method without determining the level, abundance, concentration, and/or identity of any of the plurality of species prior to exposing the plurality of species to the aqueous partitioning system.

24. The method of claim 18, comprising performing the method without using information related to the level, abundance, concentration, and/or identity of any of the plurality of species prior to exposing the aqueous partitioning system.

25. The method of claim 18, comprising performing the method without determining the identity of at least one of the species in the plurality of species prior to or after exposing the at least one species to the aqueous partitioning system.

26. The method of claim 18, comprising performing the method without determining the level, abundance, concentration, and/or identity of any of the plurality of species prior to or after exposing the plurality of species to the aqueous partitioning system.

27. The method of claim 18, comprising performing the method without using information related to the level, abundance, concentration, and/or identity of any of the plurality of species prior to or after exposing the plurality of species to the aqueous partitioning system.

28. The method of claim 18, comprising:
    comparing the first data pattern and the second data pattern to define a comparative pattern; and
    comparing the comparative pattern to a reference pattern to determine the at least one characteristic.

29. The method of claim 18, wherein the plurality of species partitions between the first and second phases on the basis of structural differences.

30. The method of claim 18, comprising comparing at least a portion of the first data pattern with at least a portion of the second data pattern to determine a condition of a biological system.

31. The method of claim 18, wherein the second data pattern is representative of a sample indicative of an unknown condition of an organism.

32. The method of claim 18, wherein the method is performed without determining the chemical or biological identity of any of the plurality of species.

* * * * *